United States Patent
Chatterjee

(10) Patent No.: US 6,228,889 B1
(45) Date of Patent: May 8, 2001

(54) METHODS FOR TREATMENT OF CONDITIONS ASSOCIATED WITH LACTOSYLCERAMIDE

(75) Inventor: Subroto Chatterjee, Columbia, MD (US)

(73) Assignee: Johns Hopkins University, Baltimore, MD (US)

(*) Notice: Subject to any disclaimer, the term of this patent is extended or adjusted under 35 U.S.C. 154(b) by 0 days.

(21) Appl. No.: 09/340,341

(22) Filed: Jun. 25, 1999

Related U.S. Application Data

(62) Division of application No. 08/998,262, filed on Dec. 24, 1997, now Pat. No. 5,972,928.
(60) Provisional application No. 60/047,249, filed on May 21, 1997.

(51) Int. Cl.[7] .......................... A61K 31/16; C07C 233/01
(52) U.S. Cl. ............................. 514/629; 564/224
(58) Field of Search ..................... 514/625, 627, 514/629, 237.8, 331, 428; 424/9.2; 564/224

(56) References Cited

U.S. PATENT DOCUMENTS

| | | | |
|---|---|---|---|
| 5,041,441 | * 8/1991 | Radin et al. | 514/237.08 |
| 5,302,609 | 4/1994 | Shayman et al. | 514/380 |
| 5,707,649 | 1/1998 | Inokuchi et al. | 424/450 |

OTHER PUBLICATIONS

The Merck Index, Eleventh Edition (1989).
A. Bhunia et al., *J. Bio. Chem.*, 272:15642–45649 (1997).
S. Chatterjee et al., *Glycobiology*, pp. 303–311 (1996).
N. Radin et al., *Adv. in Lipid Res.*, 26:183–213 (1993).
C. Rani et al., *J. Biol. Chem.*, 270:2859–2867 (1995).
A. Abe et al., *Biochimica et Biophysica Acta*, 1299:333–341 (1996).
G. Shukla et al., *Biochimica et Biophysica Acta*, 1083:101–108 (1991).
J. Inokuchi et al., *J. Lipid Res.*, 28:565–571 (1987).
A. Shukla et al., *J. Lipid Res.*, 32:713–722 (1991).
J. Tardif et al., *New Eng. J. Med.*, 337:365–372 (1997).
A. Abe et al., *J. Lipid Res.*, 36:611–621 (1995).
S. Chatterjee, *Mol. Cell Biochem.*, 111(1–2):143–147 (1192).
S. Chatterjee et al., *Glycobiology*, 7:57–65 (1997).
S. Chatterjee et al., *J. Lipid Res.*, 37:1334–1344 (1996).
N. Radin, *Mol. & Chem. Neuropathology*, 21:111–127 (1994).
T. Hanichen et al., *Laboratory Animal Sci.*, 47:275–279 (1997).
S. Chatterjee, *Biochemical & Biophysical Res. Comm.*, 181:554–561 (1991).
N Radin et al., *Advances in Lipid Res.*,26:183–213 (1993).

* cited by examiner

Primary Examiner—Floyd D. Higel
Assistant Examiner—Ebenezer Sackey
(74) Attorney, Agent, or Firm—Peter F. Corless; Kerri Pollard Schray; Robert L. Buchanan

(57) ABSTRACT

The present invention includes methods for treatment and prophylaxis of diseases, post-surgical disorders and bacterial infections associated with lactosylceramide. The methods generally provide for administration for a mammal, particularly a human, of a therapeutically effective amount of a compound that inhibits UDPGal:GlcCerβ1->4 galactosylceramide (GalT-2). In vitro and in vivo assays for detecting compounds with therapeutic capacity to modulate GalT-2 are also provided.

8 Claims, 27 Drawing Sheets

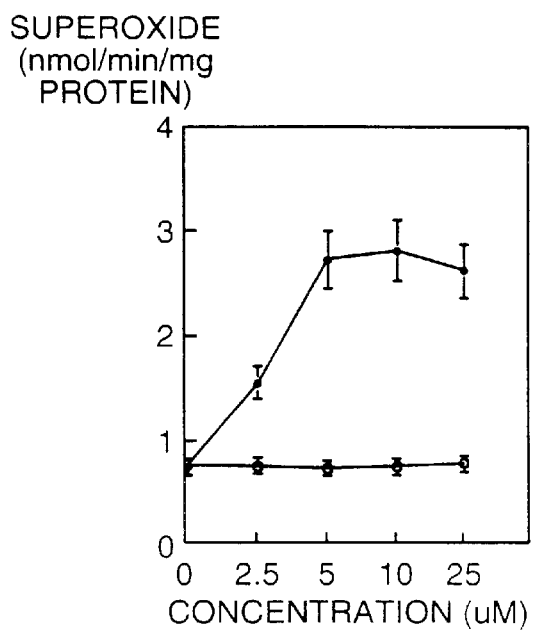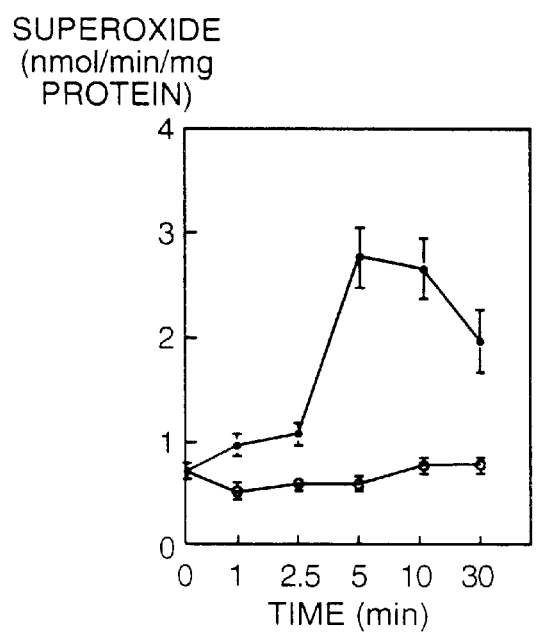
FIG. 3A     FIG. 3B
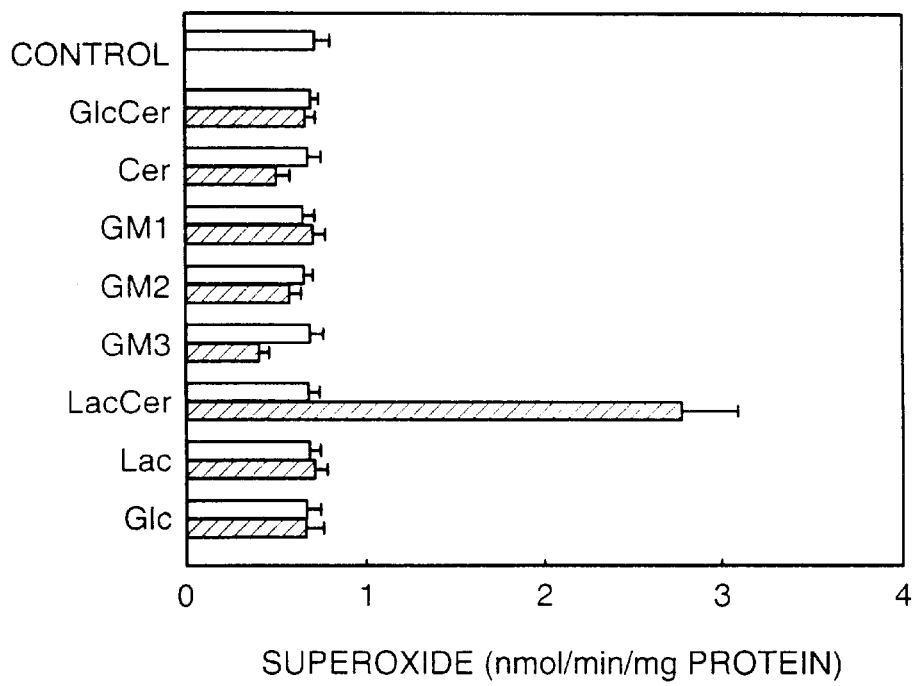
FIG. 3C

Control

LacCer

NAC + LacCer

DPI + Lac Cer

METHODS FOR TREATMENT OF CONDITIONS ASSOCIATED WITH LACTOSYLCERAMIDE

CROSS REFERENCE TO RELATED APPLICATIONS

The present application is a continuation-in-part of co-pending U.S. provisional application Ser. No. 60/047,249, filed May 21, 1997, and which is incorporated herein by reference in its entirety which is a division of 08/998,262 now U.S. Pat. No. 5,972,928.

BACKGROUND OF THE INVENTION

1. Field of the Invention

The present invention includes methods for treating conditions modulated by lactosylcerarnide and, more particularly, to the use of one or more compounds that inhibit UDP-galactose, GicCer, 1->4 galactosyltransferase (GalT-2) to treat a subject suffering from or susceptible to a condition caused or contributed to by lactosylceramide. The present invention also relates to methods for detecting and analyzing compounds with therapeutic capacity to treat such conditions.

2. Background

Uncontrolled cell proliferation relates to conditions impacting the heart, kidney, liver and other organs. For example, uncontrolled cell proliferation is indicative of diseases such as certain vasculopathies, e.g., atherosclerosis, and pathologies involving neovascularization, tumor or cyst development, e.g., polycystic kidney disease and post-surgical keloid formation. In particular, uncontrolled proliferation of vascular cells can significantly contribute to disease by occluding blood flow and enhancing vessel remodeling. Certain post-surgical disorders such as restenosis are particularly affected by uncontrolled vascular cell proliferation. See generally *Harrison's Principles of Internal Medicine*, (1991) 12$^{th}$ ed. McGraw-Hill, Inc.; and Cole, B. R. (1990) in *The Cystic Kidney*, Dordrecht, Netherlands.

Invasive surgical procedures have been developed to alleviate certain diseases and post-surgical disorders. For example, certain surgical techniques involving angioplasty, and particularly balloon angioplasty, have been developed to enhance vascular flow. However, angioplast is often accompanied by side effects such as restenosis. In particular, restenosis is recognized as a serious post-surgical complication of angioplasty. See Landau, C., et al. (1994) *N. Eng. J. Med*, 330:981 and references cited therein.

Further attempts to alleviate diseases and post-surgical disorders impacted by uncontrolled cell proliferation have employed certain therapeutic agents. For example, there has been much effort to develop agents that can reduce restenosis after angioplasty. More specifically, probucol is a recognized therapeutic agent that has been reported to reduce restenosis in some patients. However, existing probucol-based therapies are believed to be ineffective due to unsatisfactory patient tolerance and insufficient reduction of stenoses. See e.g., Tardif, J. C. et al., (1997) *N. Eng. J Med,* 337:365–372; Ferns, G. A. A. et al. (1992) *PNAS* (USA) 89:11312 and references cited therein.

Efforts have been made to develop therapies that treat or prevent conditions affected by cell proliferation. For example, one approach has been to identify agents with therapeutic capacity to modulate cell pathways involving glycosphingolipids (GSLs). The GSLs are believed to impact lipid storage diseases, particularly glycosphingolipidoses and perhaps other lipid-related pathologies. See e.g., Chatterjee, S., *Biochem. Biophys. Res Comm.* (1991) 181:554; Hakomori, S. I. (1983) in *Sphingolipid Chemistry*, eds. Kanfer, J. N. and Hakomori, S. I. (Plenum Press, New York) and references cited therein.

Certain biochemical steps relating to GlcCer and LacCer have been disclosed. For example, one step involves synthesis of GIcCer by coupling UDP-glucose to ceramide in a reaction catalyzed by UDP-glucose glucosyltransferase (GlcT-1). Another step converts the GicCer to LacCer using UDP-galactose, GicCer, β1->4 galactosyltransferase (GalT-2). See eg., Chatterjee et al. supra Attempts have been made to inhibit biochemical steps involving GlcT-1. For example, it has been reported that D-1-phenyl-2-decanolylamino-3-morpholino-1-propanol (D-PDMP) inhibits GlcT-1 and reduces proliferation of vascular cells. The mechanism of PDMP has been reported to be unclear. See e.g., Felding-Habermann, B., et al. (1991) *Biochemistry* 29:6314; Shukla, G. S. et al. *Biochem. Biophys. Acta* (1991) 1083:101; Inokuchi, J. et al., *J. Lipid Res.* (1987) 28:565; Chatterjee, S., supra.

Specified morpholinoceramides also have been disclosed as GlcT-1 inhibitors. See Carson, K. and B. Ganem (1994) *Tetrahedron Lets.* 35:2659.

Other cell functions are believed to play a role in conditions modulated by LacCer. For example, uncontrolled cell adhesion is believed to effect specified immune responses such as allergic reactions and host rejection of foreign tissue.

It has been reported that uncontrolled cell proliferation and cell adhesion can affect certain vasculopathies. For example, atherosclerosis is believed to be worsened by adhesion of certain immune and vascular cells. Plaque formation is particularly enhanced by cell proteins such as intercellular adhesion molecule-1 (ICAM-1, CD54) and vascular cell adhesion molecule-1 (VCAM-1). See e.g., Kume, N. et al. (1992) *J. Clin. Invest.* 90:1138; Iademarco, M. F. et al. (1995) *J. Clin. Invest.* 95:264; Carlos, T. et al. *Blood* (1991) 77:2266; Nagel, T. et al. (1994) *J. Clin. Invest.* 94:885; and Cybulsky, M. I. and Gimbrone M. A. (1991) *Science* 251:788.

Certain GSLs also have been reported to be cell receptors for bacterial toxins. For example, cellular uptake of cholera toxin is believed to be enhanced by a membrane-associated GSLS.

Thus, it would be desirable to have additional methods of treating conditions or diseases modulated by lactosylceramides, e.g. to inhibit GalT-2, in order to treat or prevent such conditions.

SUMMARY OF THE INVENTION

We have now discovered therapies to treat or prevent various diseases, post-surgical disorders and bacterial infections modulated by lactosylceramide (LacCer). In particular, we have discovered therapies that include altering activity of UDP-galactose, GlcCer, β1->4 galactosyl-transferase (GalT-2).

More specifically, the invention provides methods for treatment of proliferative disorders such as vasculopathies, e.g. atherosclerosis and restenosis; pathologies involving neovascularization; tumor or cyst development, e.g., polycystic kidney disease and post-surgical keloid formation; inflammatory diseases involving a proinflammatory cytokine such as TNF-α or interleukin-6; and lipid storage diseases such as Gaucher's disease.

Therapies of the invention are particularly effective for the treatment and prevention of undesired vascular restenoses. In one protocol of the invention, a near absence of intimal proliferation was observed at the site of balloon angioplasty in the test subject (rabbit), whereas a control subject exhibited significant intimal proliferation. See the results set forth in the examples which follow.

LacCer-modulated diseases that can be treated in accordance with the invention also include lipid storage diseases (i.e. glycospingolipodoses) such as Gaucher's disease, cholesterol storage disease and the like.

Additional disorders that can be treated in accordance with the invention include bacterial infections, particularly those infections involving production of a toxin, such as an exotoxin that can specifically bind LaCer, e.g. *Neisseria gonorrhoeae*. See Paruchuri, D. K. et al. (1990) *Proc. Natl. Acad. Sci.* (USA), 87:333–337.

Therapeutic methods of the invention in general comprise administering to a subject, particularly a mammal such as a primate, especially a human, a therapeutically effective amount of a compound that can inhibit GalT-2 activity. Preferably, an administered compound inhibits cell proliferation by at least about 15% or 25% in a standard in vitro cell proliferation assay. Examples of such an assay are described below. It is generally preferred that the administered compound exhibits an $IC_{50}$ of at least about 500 $\mu$M in a standard in vitro GalT-2 assay as defined below, more preferably an $IC_{50}$ of about 100 $\mu$M or less, still more preferably an $IC_{50}$ of about 1–10 $\mu$M or less in a standard in vitro GalT-2 assay as defined below. Such compounds that can inhibit GalT-2 activity are generally referred to herein as "GalT-2 inhibitor compounds" or other similar term.

Compounds suitable for use in the treatment methods of the invention include those of the following Formula I:

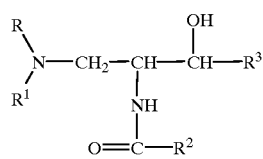

wherein R, $R^1$, $R^2$ and $R^3$ are as defined below; and pharmaceutically acceptable salts of such compounds.

Specifically preferred inhibitor compounds for use in the therapeutic methods of the invention include:

1-phenyl-2-decanoylamino-3-morpholino-1-propanol;

1-phenyl-2-hexadecanoylamino-3-morpholino-1-propanol;

1-phenyl-2-hexadecanoylamino-3-piperidino-1-propanol;

1-phenyl-2-hexadecanoylamino-3-pyrrolidino-1-propanol;

1-morpholino-2-hexadecanoylamino-3-hydroxyoctadec4,5-ene; and 1-pyrrolidino-2-hexadecanoylamino-3-hydroxyoctadec4,5-ene.

Especially preferred inhibitor compounds for use in the methods of the invention are (1R,2R)1-phenyl-2-decanoylamino-3-morpholino-1-propanol (D-PDMP) and trans-(2R3R)-1-pyrrolidino-2-hexadecanoylamino-3-hydroxyoctadec4,5-ene.

Other suitable GalT-2 inhibitor compounds can be readily identified by simple testing, e.g. by in vitro testing of a candidate inhibitor compound relative to a control for the ability to inhibit GalT-2 activity, e.g. by at least 10% more than a control.

The invention further relates to methods of detecting and analyzing compounds that inhibit GalT-2 and exhibit therapeutic capacity to treat or prevent the above-described conditions. Preferred detection and analysis methods include both in vitro and in vivo assays to determine the therapeutic capacity of agents to modulate LacCer-responsive cells.

Preferred in vitro detection assays according to the present invention involve one or more steps associated with LacCer-related pathways. Such assays include the following steps 1) through 4):

1) culturing a population of LacCer-responsive cells with LacCer;
2) adding a known or candidate GalT-2 inhibitor compound to the cells;
3) measuring activity of a specified cell molecule in the LacCer-related step;
4) determining the effect of the known or candidate GalT-2 inhibitor compound on the cell, such as cell proliferation, adhesion or expression of surface proteins.

That assay can effectively measure the capacity of the GalT-2 inhibitor compound to decrease GalT-2 activity. References herein to a "standard in vitro GalT-2 assay" or other similar phrase refers to the above protocol of steps 1) through 4) when the specified cell molecule measured in step 3) above is GalT-2. As described in more detail below, other in vitro assays of the invention measure additional specified cell molecules in the LacCer-related steps or pathways. The in vitro assays of the present invention can be conducted with nearly any population of cells responsive to LacCer including a lysate of such cells or tissue, or a substantially purified fraction of the lysate. Suitable LacCer responsive cells that may be employed in the assay include, e.g., cells associated with vascular intima, particularly primary and/or immortalized endothelial and smooth muscle cells, as well as certain immune cells such as leukocytes. Preferred LacCer lysates or subcellular fractions include GalT-2.

The in vitro detection assays of the invention can be adapted in accordance with intended use. For example, as noted above, it has been found that LacCer manifests changes in certain cell functions such as cell proliferation and adhesion. Thus, the standard in vitro assay above can be modified at step 3) to include measuring cell proliferation or adhesion in response to the added LacCer, and to determine any effect of the GalT-2 inhibitor compound on the cell function. The known or candidate GalT-2 inhibitor compound tested in the assays can be employed as a sole active agent or in combination with other agents including other GalT-2 inhibitor compounds to be tested. In most instances, the in vitro assays are performed with a suitable control assay usually comprising the same test conditions as in the steps above, but without adding the GalT-2 inhibitor compound to the medium. In such cases, a candidate GalT-2 inhibitor compound can be identified as exhibiting desired activity by exhibiting at least about 10 percent greater activity relative to the control; more preferably at least about 20% greater activity relative to the control assay; and still more preferably at least about 30%, 40%, 50%, 60%, 70, 80%, 100%, 150% or 200% greater activity relative to the control.

The invention also provides assays to detect a LacCer-responsive cell which cells may be used, e.g., in an assay of the invention as described above. For example, a potentially LacCer-responsive cell can be contacted by LacCer and then a desired cell molecule or function in a LacCer-related protein as discussed previously is measured as a function of the amount of LacCer added. In most cases, the cell is deemed responsive to LacCer if the assay employed shows at least about 10%, preferably at least about 20%, more preferably at least about 50%, and still more preferably at least about 75% or 100% change in the activity (relative to a control) of the molecule or cell function as determined by the assays provided herein. The assays can be used to identify LacCer-responsiveness in a variety of cells or tissues, including cultured cells (i.e., primary cells or immortalized cell lines) and organs.

The invention also provides in vivo assays to determine the therapeutic capacity of a known or candidate GalT-2 inhibitor compound to modulate cell functions impacted by LacCer, e.g. cell proliferation and adhesion. The monitored cell function suitably may be pre-existing in the test animal, or the cell function may be induced, e.g., by an invasive surgical procedure such as angioplasty. Cell functions that can be suitably assayed in these methods include, e.g., vascular cell proliferation and adhesion as well as vessel remodeling.

The in vivo assays of the present invention can be modified in a number of ways as needed. For example, in certain embodiments of the present invention, the vessel subjected to analysis is assayed in vitro following removal from the animal or assayed in vivo if desired. In other embodiments, the GalT-2 inhibitor compound is administered to the animal either as a sole active agent or in combination with other active compounds (e.g., probucol), including other GalT-2 inhibitor compounds to be tested. In most embodiments, activity of the GalT-2 inhibitor compound in a given in vivo assay is compared to a suitable control (e.g., a sham-operated animal) in which the assay is conducted the same as the test assay but without administering the GalT-2 inhibitor compound to the test subject. A variety of test subjects can be employed, particularly mammals such as rabbits, primates, various rodents and the like.

As noted above, the detection assays (either in vitro or in vivo) can be conducted in a wide variety of LacCer-responsive cells, tissues and organs. Further, the assays can detect useful GalT-2 inhibitor compounds by measuring the activity of target molecules and functions in LacCer-related pathways. Thus, the present assays can measure activity in several cell, tissue and organ settings.

Significantly, use of multiple detection assays (e.g., a combination of the in vitro and/or in vivo assays) with a single GalT-2 inhibitor compound can extend the selectivity and sensitivity of detection as desired.

Such broad spectrum testing provides additional advantages. Thus, for example, in vitro assays of the invention can efficiently perform multiple analyses, thereby enhancing efficiency and probability of identifying GalT-2 inhibitor compounds with therapeutic capacity. This is especially useful when large numbers of compounds need to be tested. For instance, libraries of GalT-2 inhibitor compounds can be made by standard synthetic methods including combinatorial-type chemistry manipulations and then tested in accord with the invention.

Additionally, many of the LacCer-related steps are "downstream" of GalT-2, and therefore the assays include molecules and cell functions that are active downstream of GalT-2. Accordingly, modest but significant changes in GalT-2 activity can be registered as readily testable signals.

Other aspects of the invention are discussed below.

BRIEF DESCRIPTION OF THE DRAWINGS

FIGS. 3A–C are graphs showing that LacCer stimulates superoxide generation in Eahy 926 cells (a human endothelial cell line).

DETAILED DESCRIPTION OF THE INVENTION

Figure 1:
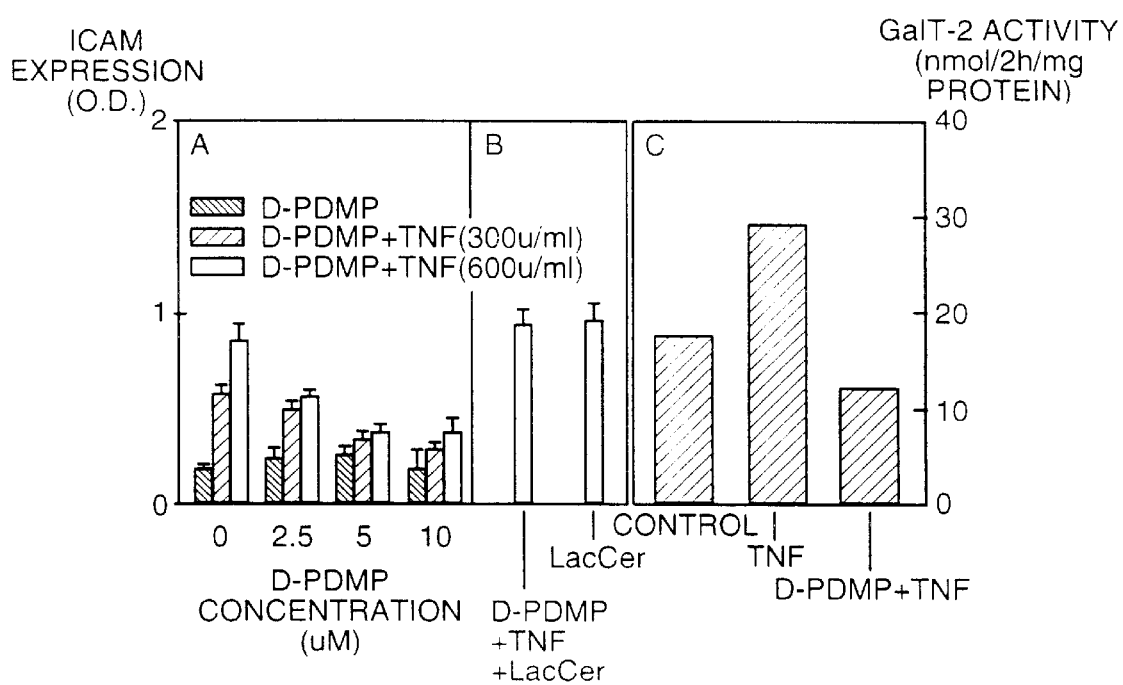
FIGS. 1A–C are graphs illustrating effects of D-PDMP on tumor necrosis factors (TNF-α) induced ICAM-1 expression and GalT-2 activity in endothelial cells.

As discussed above, the present invention features therapeutic methods for treatment and prevention of conditions modulated by LacCer. The treatment methods of the invention generally include administering a therapeutically effective amount of a GalT-2 inhibitor compound to a subject, preferably a patient in need of such treatment.

It also has been unexpectedly found that LacCer is a cell signaling molecule that can modulate various diseases, post-surgical disorders and bacterial infections. That is, changes in cell levels of LacCer alter the development or severity of those diseases, post-surgical disorders and bacterial infections. More particularly, it has been unexpectedly found that in LacCer-responsive cells, LacCer functions as a signal molecule to effect changes in certain cell steps (sometimes referred to herein as "LacCer-related steps" or "LacCer-related pathways"). LacCer-related pathways impact a variety of functions such as cell proliferation, cell adhesion and bacterial infection of cells.

The therapeutic methods of the invention generally comprise administration of a therapeutically effective amount of a GalT-2 inhibitor compound to a subject in need of such treatment, such as a mammal, and particularly a primate such as a human. Treatment methods of the invention also comprise administration of an effective amount of a compound of Formula I as defined herein to a subject, particularly a mammal such as a human in need of such treatment for an indication disclosed herein.

Typical subjects include mammals suffering from or susceptible to those conditions discussed above, i.e. proliferative disorders such as vasculopathies, e.g. atherosclerosis and restenosis such as may occur following an angioplasty procedure; pathologies involving neovascularization; tumor or cyst development, e.g., polycystic kidney disease and post-surgical keloid formation such as may occur on the skin of a patient; inflammatory diseases involving a proinflammatory cytokine such as TNF-α or interleukin-6 (IL-6); and lipid storage diseases such as Gaucher's disease.

A variety of GalT-2 inhibitor compounds can be employed in the present treatment methods Simple testing, e.g., in a standard in vitro assay as defined above, can readily identify suitable GalT-2 inhibitor compounds. Preferred GalT-2 inhibitor compounds include those that contain a propanol backbone. Generally preferred for use in the treatment methods of the invention are compounds of the following Formula I:

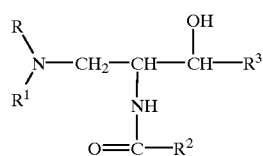

wherein R and $R^1$ are independently selected from the group consisting of hydrogen and straight-chained or branched $C_1$–$C_6$ alkyl with or without a substituent such as amino, hydroxy or mercapto and further wherein R and $R^1$ may be taken together to form a 5, 6 or 7-membered ring substituent such as pyrrolidino, morpholino, thiomorpholino, piperidino, azacycloheptyl and the like;

$R^2$ is selected from the group consisting of branched or straight-chained $C_6$–$C_{30}$ alkyl with or without one to three double bonds; and $R^3$ is selected from the group consisting of straight-chained or branched $C_6$–$C_{20}$ alkyl with or without one to three double bonds and aryl such as carbocyclic aryl (e.g., phenyl), or substituted aryl such as carbocyclic aryl (e.g., phenyl), where the substituent is halo, $C_1$–$C_4$ alkoxy, methylenedioxy, $C_1$–$C_4$ mercapto, amino or substituted amino in which the amino substituents may suitably be $C_1$–$C_4$ alkyl.

Suitable compounds of Formula I above and other GalT-2 inhibitor compounds can be readily prepared by known procedures or can be obtained from commercial sources. See, for example, Abe, A. et al., (1992) *J. Biochem.* 111:191–196; Inokuchi, J. et al. (1987) *J. Lipid Res.* 28:565–571; Shukla, A. et al. (1991) *J. Lipid Res.* 32:73; Vunnam, R. R. et al., (1980) *Chem. and Physics of Lipids* 26:265; Carson, K. et al., (1994) *Tetrahedron Lets.* 35:2659; and Akira, A. et al., (1995) *J. Lipid Research* 36:611.

In the therapeutic methods of the invention, a treatment compound can be administered to a subject in any of several ways. For example, a GalT-2 inhibitor compound can be administered as a prophylactic to prevent the onset of or reduce the severity of a targeted condition. Alternatively, a GalT-2 inhibitor compound can be administered during the course of a targeted condition.

A treatment compound can be administered to a subject, either alone or in combination with one or more therapeutic agents, as a pharmaceutical composition in mixture with conventional excipient, i.e. pharmaceutically acceptable organic or inorganic carrier substances suitable for parenteral, enteral or intranasal application which do not deleteriously react with the active compounds and are not deleterious to the recipient thereof Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl- cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Such compositions may be prepared for use in parenteral administration, particularly in the form of liquid solutions or suspensions; for oral administration, particularly in the form of tablets or capsules; intranasally, particularly in the form of powders, nasal drops, or aerosols; vaginally; topically e.g. in the form of a cream; rectally e.g. as a suppository; etc.

The pharmaceutical agents may be conveniently administered in unit dosage form and may be prepared by any of the methods well known in the pharmaceutical arts, e.g., as described in *Remington's Pharmaceutical Sciences* (Mack Pub. Co., Easton, Pa., 1980). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain GalT-2 inhibitor compounds.

Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration. Other delivery systems will administer the therapeutic agent(s) directly at a surgical site, e.g. after balloon angioplasty a GalT-2 inhibitor compound may be administered by use of stents.

A GalT-2 inhibitor compound can be employed in the present treatment methods as the sole active pharmaceutical agent or can be used in combination with other active ingredients, e.g., probucol, known antioxidants (e.g Vitamin C or E) or other compounds.

The concentration of one or more treatment compounds in a therapeutic composition will vary depending upon a number of factors, including the dosage of the GalT-2 inhibitor compound to be administered, the chemical characteristics (e.g., hydrophobicity) of the composition employed, and the intended mode and route of administration. In general terms, one or more than one of the GalT-2 inhibitor compounds may be provided in an aqueous physiological buffer solution containing about 0.1 to 10% w/v of a compound for parenteral administration.

It will be appreciated that the actual preferred amounts of active compounds used in a given therapy will vary according to e.g. the specific compound being utilized, the particular composition formulated, the mode of administration and characteristics of the subject, e.g. the species, sex, weight, general health and age of the subject. Optimal administration rates for a given protocol of administration can be readily ascertained by those skilled in the art using conventional dosage determination tests conducted with regard to the foregoing guidelines. Suitable dose ranges may include from about 1 µg/kg to about 100 mg/kg of body weight per day.

Therapeutic compounds of the invention are suitably administered in a protonated and water-soluble form, e.g., as a pharmaceutically acceptable salt, typically an acid addition salt such as an inorganic acid addition salt, e.g., a hydrochloride, sulfate, or phosphate salt, or as an organic acid addition salt such as an acetate, maleate, fumarate, tartrate, or citrate salt. Pharmaceutically acceptable salts of therapeutic compounds of the invention also can include metal salts, particularly alkali metal salts such as a sodium salt or potassium salt; alkaline earth metal salts such as a magnesium or calcium salt; ammonium salts such an ammonium or tetramethyl ammonium salt; or an amino acid addition salts such as a lysine, glycine, or phenylalanine salt.

Preferred GalT-2 inhibitor compounds exhibit significant activity in a standard cell proliferation assays. Preferably, the GalT-2 inhibitor compound inhibits cell proliferation by at least 15 or 25%, preferably at least 50%, relative to a suitable control assay. In such an assay, between about 0.1 to 100 µM, preferably between about 1 to 50 µM of a desired GalT-2 inhibitor compound is used. Exemplary cell proliferation assays include counting viable cells and monitoring activity of specified citric acid cycle enzymes such as lactate dehydrogenase. A preferred assay measures incorporation of one or more detectably-labeled nucleosides into DNA, e.g., by:

a) culturing suitable cells in medium and adding 1) a candidate GalT-2 inhibitor compound and 2) a radio-labeled nucleoside such as $^3$H- thymidine typically in an amount between about 0.1 to 100 µCi;

b) incubating the cells, e.g., for about 6–24 hours, and typically followed by washing; and c) measuring incorporation of the radiolabeled nucleoside into DNA over that time relative to a control culture that is prepared and incubated under the same conditions as the assay culture but does not include the potential GalT-2 inhibitor compound. The measurement can be achieved by several methods including trichloroacetic acid (TCA) precipitation of labeled DNA on filters followed by scintillation counting. See e.g., Chatterjee, S., *Biochem. Biophys. Res Comm.* (1991) 181:554; Chatterjee, S. et al. (1982) *Eur. J Biochem.* 120:435 for disclosure relating to this assay.

References herein to a "standard in vitro cell proliferation assay" or other similar phrase refer to an assay that includes the above steps a) through c). One preferred example of a cell proliferation assay uses aortic smooth muscle cells (ASMCs), particularly those obtained from a human, cow or a rabbit. A suitable protocol involves preparing ASMCs according to standard methods and culturing same in microtitre plates in a suitable medium such as Ham's F-10. A desired GalT-2 inhibitor compound is then diluted in the medium, preferably to a final concentration of between about 1 to 100 µg, more preferably between about 1 to 50 µg per ml of medium or less followed by an incubation period of between about 1–5 days, preferably about 1 day or less. Following the incubation, a standard cell proliferation can be conducted, e.g., incorporation of tritiated thymidine or lactate dehydrogenase assay as mentioned above. The assays are preferably conducted in triplicate with a variation of between 5% to 10%. See e.g, Ross, R. *J. Cell Biol.* (1971) 50:172; Chatterjee, S. et al. (1982) *Eur. J. Biochem.* 120:435; Bergmeyer, H. V. *In Principles of Enymatic Analysis.* (1978) Verlag Chemie, N.Y.

Additionally, preferred GalT-2 inhibitor compounds exhibit significant activity in a conventional cell adhesion assay. Preferably, the GalT-2 inhibitor compound inhibits cell adhesion by at least 25%, preferably at least 50% or more relative to a suitable control assay. In such an assay, between about 0.1 to 50%, preferably between about 1 to 50 µM of a desired GalT-2 inhibitor compound is used. For example, a preferred cell adhesion assay includes the following steps:

a) labeling a first population of immune cells, preferably certain leukocytes, with a detectable label which can be a chromatic, radioactive, luminescent (e.g., fluorescent, or phosphorescent), or enzymatic label capable of producing a detectable label, b) contacting the first population of cells with a second population of endothelial cells detectably-labeled, e.g., with a chromatic, radioactive, luminescent (e.g., fluorescent or phosphorescent), or enzymatic label preferably different from the label employed in step a); and c) detecting any adhesion between the first and second population of cells.

References herein to a "standard in vitro cell adhesion assay" or other similar phrase refer to an assay that includes the above steps a) through c). The detection in step c) can be achieved by a variety of methods such as microscopy, particularly confocal microscopy and fluorescence-based photomicroscopy involving FACS; automated cell sorting techniques, immunological methods such as ELISA and RIA; and scintillation counting. See examples below for disclosure relating to preferred cell adhesion assays.

A preferred in vitro cell adhesion assay measures polymorphonuclear leukocytes (PMNs and/or myocytes) or platelets and increased endothelial cell adhesion before, during or after contact with a desired GalT-2 inhibitor compound. The PMNS or myocytes can be collected and purified according to standard methods detailed below. The PMNs or myocytes are then labeled by incubation with a suitable fluorescent dye such as fluorescent Cell Tracker dye (e.g., green) or Calcein-AM. At about the same time, an endothelial cell monolayer prepared in accordance with standard cell culture methods on a suitable substrate such as a slide or a sterilized plastic petri dish is contacted by the GalT-2 inhibitor compound and labeled with another fluorescent dye such as fluorescent Cell Tracker dye (e.g., orange). The PMNs or myocytes and endothelial cells are then incubated for between about 10 minutes to a few hours, preferably about 30 minutes at 37° C. Non-adherent cells are then washed away from the slide with a physiologically acceptable buffer such as phosphate-buffered saline (PBS). Adhering cells are then quantitated by standard methods such as by use of a fluorescence plate reader. The number of adherent cells on the slide can be quantitated in several ways including expressing the number of PMN/mm$^2$ on the endothelial cell monolayer. Alternatively, the adhering cells can be quantitated by inspection following photomicroscopy visualized and photographed by microscopy. Cell adherence is then evaluated by inspection of the photomicrograph. See the examples which follow.

Particularly preferred are GalT-2 assays conducted with the ASMCs and performed in accordance with previously described methods. See e.g., Chatterjee, S., and Castiglione, E. (1987) *Biochem. Biophys. Acta,* 923:136; and Chatterjee, (1991) S. *Biochem. Biophys. Res Comm.,* 181:554.

Additionally preferred in vitro cell adhesion assays include immunological detection of adhesion molecules on PMNs using specified antibodies, particularly monoclonals, capable of specifically binding the adhesion molecules. A particularly preferred assay involves flow cytometry.

The in vitro adhesion assays described above are compatible with analysis of a variety of specified adhesion molecules such as ICAM-1 (intracellular adhesion molecule 1), Mac-l (CD11b/CDI8), LFA-1 and selectin.

Another preferred assay of the invention includes the following steps a) through d):

a) culturing a population of LacCer-responsive cells preferably to confluency in lipoprotein-deficient serum medium, e.g., about 1 mg lipoprotein-deficient serum/protein/ml of medium or less;

b) harvesting the cells preferably in a suitable dispersive buffer, e.g., cacodylate buffer, c) incubating the harvested cells preferably with a detectably labeled molecule such as a detectably-labeled nucleoside diphosphate sugar donor such as [$^{14}$C]-UDP-galactose typcially in an amount between about 0.1 to 100 μCi; and d) measuring LacCer formation as indicative of the activity of the GalT-2 enzyme.

In most instances, the assays generally described above will use known LacCer-responsive cells and will be cultured in a medium suitable for maintaining those cells in the assay, e.g., Eagles's minimum essential medium (HMEM) or Ham's F-10 medium.

Further preferred GalT-2 inhibitor compounds include those that exhibit at least ;a 2- to 5-fold greater inhibition of GalT-2 relative to GlcT-1 as measured by conventional GlcT-1 and GalT-2 enzyme assays. More preferred are those GalT-2 inhibitor compounds that exhibit at least about 5- to 10-fold greater inhibition of GalT-2 relative to inhibition of GlcT-1, even more preferably at least about 10- to 50-fold. Methods for measuring GlcT-1 have been reported. See e.g., Carson, K., and Ganem, B. supra; Shukla, A. and Radin, N. S. *J. Lipid Res.* 32:713.

Particularly preferred GalT-2 inhibitor compounds include those that are capable of specifically inhibiting the GalT-2 enzyme. That is, the identified GalT-2 inhibitor compound is a relatively poor inhibitor of other enzymes relating to GSLs such as hydroxyceramide galactosyltransferase, glucocerebroside glucosidase, and particularly GlcT-1. Significantly, the GalT-2 inhibitor compound should avoid undesired pharmacological effects that could arise from non-selective inhibition of other GSL-related enzymes. Exemplary of such preferred GalT-2 inhibitor compounds are those which are GalT-2 transition state mimics.

The in vivo assays of the invention are particularly useful for subsequent evaluation of GalT-2 inhibitor compounds exhibiting suitable activity in an in vitro assay. A rabbit model of restenosis accompanying an invasive surgical procedure such as balloon angioplasty is preferred. One suitable protocol involves administering to the rabbit a suitable vehicle or vehicle combined with one or more GalT-2 inhibitor compounds of interest. The amount of the GalT-2 inhibitor compound administered will vary depending on several parameters including the extent of damage associated with the surgical procedure of interest. In instances where balloon angioplasty is employed, the rabbit will typically receive a candidate GalT-2 inhibitor compound in a dose (e.g., i.m. or i.p.) of between about 0.5 to 100, preferably 1 to 20 and more preferably about 10 mg/kg body weight of the rabbit. A preferred dosage schedule provides for administration of a GalT-2 inhibitor compound starting 24 hurs prior to conducting an invasive surgical procedure, and then continuing administration of the GalT-2 inhibitor compound for 15 days following the surgical procedure. In other protocols, daily injections of the GalT-2 inhibitor compound may be made for about 2 to 12 weeks following the invasive surgical procedure. Daily injections, e.g., i.m. or i.p., of the GalT-2 inhibitor compound are generally preferred. Subsequently, the rabbits are euthanized and a vessel removed for examination, preferably the aorta The vessel is then fixed with formalin and analyzed for proliferation of vascular endothelia, media and advantitia using standard histological procedures.

The term "invasive surgical procedure" means a medical or veterinary technique associated with significant damage to the endothelium of a vessel impacting e.g., an organ such as the heart, liver or the kidney, or a limb. Such a vessel comprises the aorta, coronary vessel, femoral and iliac arteries and veins. The invasive surgical procedure can be associated with techniques involving, e.g., cardiac surgery, abdominothoracic surgery, arterial surgery, deployment of an implementation (e.g., a vascular stent or catheter), or endarterectomy. A preferred invasive surgical procedure is angioplasty, particularly balloon angioplasty. Preferably, the invasive surgical procedure is performed on a mammal such as a primate, particularly a human, rodent or a rabbit, or a domesticated animal such as a pig, dog or a cat.

As noted above, the present invention includes methods of detecting and analyzing GalT-2 inhibitor compounds with therapeutic capacity to treat or prevent any of the above-mentioned diseases, post-surgical disorders, or bacterial infections modulated by LacCer. A disease, post-surgical disorder or bacterial infection is suitably considered as being modulated by LacCer if afflicted cells or tissue exhibit GalT-2 activity about 2- to 5-fold, typically about 2- to 10-fold, and more typically about 2- to 5-fold higher than that of control (unafflicted) cells or tissue. The GalT-2 activity can be measured by methods referenced herein. Without being bound by theory, it appears that increased GalT-2 activity produces substantial amounts of LacCer. That LacCer is believed to enhance the onset of or contribute to the severity of the specified diseases, post-surgical disorders and bacterial infections. In particular, it has been reported that GalT-2 levels in renal tissue afflicted by polycystic kidney disease exhibit a 3-fold elevation in GalT-2 activity and LacCer levels as compared to control renal tissue. Accordingly, polycystic kidney disease is one example of a disease impacted by LacCer. See Chatterjee, S. et al. *J. Lipid Res.* (1996) 37:1334.

Generally stated, the novel LacCer-related steps disclosed herein have been found to relate changes in GalT-2 activity to cell proliferation or adhesion in LacCer-responsive cells. It has been determined that the LacCer-related steps can be grouped into those inhibiting cell proliferation and those effecting cell adhesion. The LacCer-related steps have been found to include a variety of identified molecules such as specified enzymes, cytosolic factors, nuclear factors, radical species and adhesion proteins. More particular examples of such molecules in the LacCer-related biochemical steps include GTP-binding proteins, kinases, cytosolic factors, nuclear factors, transcription factors, and oxygen species, particularly reactive oxygen species (sometimes referred to herein as "ROS" or "ROM").

Detection methods of the invention are formatted to include one or more steps associated with LacCer-related pathways. More particularly, the detection methods include specific steps that measure the activity of molecules which act to modulate cell proliferation or adhesion. In some cases, a particular molecule will act to inhibit both cell proliferation and adhesion through a LacCer-related pathway.

The LacCer-related steps are found in cells responsive to LacCer. A LacCer-responsive cell can be an immortalized cell line or primary culture of cells (e.g., obtained form a tissue or organ) that manifests a change in one or more specific cell molecules or functions such as proliferation or adhesion, following contact with a suitable amount of LacCer.

More specifically, one or a combination of strategies can identify a LacCer-responsive mammalian cell. For example, in one approach, about $1 \times 10^5$ cells are seeded in petri dishes in suitable growth medium. For primary cultures of cells, a desired tissue or organ is obtained from an animal and dispersed according to standard methods (e.g., by sonication, mechanical agitation, and/or exposure to dispersing agents known in the field, e.g., detergents and proteases). After one or a few days, the growth medium is removed from the petri dish and the cells washed with phosphate-buffered saline. The cells are then primed in a suitable medium for about 1 to 5 hours at which point LacCer is added to culture. The amount of LacCer added will depend on several parameters such as the particular cell or tissue type being tested. In most cases however, the LacCer will be added to the culture at a concentration of between about 1 $\mu$g to 1 mg, preferably between about 1 $\mu$g to 500 $\mu$g, and more preferably between about 1 $\mu$g to 50 $\mu$g per ml of culture medium. After exposing the cells to the LacCer for between about 1 to 60 minutes, preferably between about 1 to 10 minutes or less, the medium is removed and the cells lysed in an appropriate lysis buffer such as those described in detail below. The cells are then assayed according to any of the methods described herein for response to the added LacCer.

Particularly preferred LacCer-responsive mammalian cells include those cells associated with smooth muscle cells, e.g., cells associated with the vasculature of an organ or limb, particularly heart or kidney cells. More particularly, ASMCs (sometimes referred to herein as H-ASMCs to denote human origin) and endothelial cells. Also preferred are certain immune cells such as white blood cells, particularly PMNs and monocytes.

Preferred GalT-2 inhibitor compounds also include those that exhibit good capacity to modulate one or more specified molecules in a LacCer-related step following exposure to LacCer. Particularly preferred compounds exhibit at least 20%, preferably at least 50% and more preferably at least 90% or more of a decrease in the activity of the molecule (relative to a suitable control assay) at a concentration of between about 0.1 to 100 $\mu$g/ml, preferably between about 1 to 10 $\mu$g/ml in an in vitro detection assay. The activity of the molecules can decrease in any of several readily detectable ways including altered synthesis, degradation or storage; protein modification, e.g., phosphorylation, or through an allosteric effect as with certain enzymes.

In particular, if the molecule of interest is an enzyme, preferred GalT-2 inhibitor compounds include those that exhibit good activity in an enzyme assay as described below. Preferably, an $IC_{50}$ in such an assay is about 20 pM or less, more preferably an $IC_{50}$ about 1 $\mu$M or less.

A control experiment is generally tailored for use in a particular assay. For example, most control experiments involve subjecting a test sample (e.g., a population of LacCer-responsive cells or lysate thereof) to medium, saline, buffer or water instead of a potential GalT-2 inhibitor compound in parallel to the cells receiving an amount of test compound. A desired assay is then conducted in accordance with the present methods. Specific examples of suitable control experiments are described below.

The present detection methods also can be used to identify GalT-2 inhibitor compounds obtained from biological sources, including specified growth factors, cytokines, and lipoproteins that modulate GalT-2 activity.

The present detection methods further include assays which measure the activity of specified molecules in LacCer-related biochemical steps. The measurements can be conducted by standard laboratory manipulations such as chemiluminescence tests, thin layer chromatography (TLC) separations, nucleic acid isolation and purification, SDS-PAGE gel electrophoresis, autoradiography, scintillation counting, densitometery, Northern and Western Blot hybridization, and immunoassays (e.g., RIA and ELISA tests). See generally Sambrook et al. in *Molecular Cloning: A Laboratory Manual* (2d ed. 1989); and Ausubel et al. (1989), *Current Protocols in Molecular Biology*, John Wiley & Sons, New York for discussion relating to many of the standard methods, the disclosures of which are incorporated herein by reference.

In one aspect, the present in vitro assays measure the activity of certain enzymes in LacCer-responsive cells. The activity of the enzymes has been found to be modulated following exposure of the cells to LacCer and/or a specified GalT-2 inhibitor compound such as PDMP, oxidized lipoprotein (ox-LDL), nerve growth factor (NGF), platelet derived growth factor (PDGF), epidermal growth factor (EGF), and tumor necrosis factors (TNF-$\alpha$).

In particular, D-PDMP has been found to reduce the activity of a variety of such enzymes including specified redox enzymes, GTP-binding proteins, and kinases discussed below.

For example, one particular in vitro assay measures the activity of an oxidase capable of synthesizing an oxygen species, particularly a ROS such as superoxide. A particularly preferred enzyme is NADPH oxidase. The activity of the NADPH oxidase can be assayed by standard methods including fractionating the enzyme from cell components and then measuring the activity by enzyme assay such as those employing a standard chemiluminescence method.

Alternatively, the NADPH oxidase can be assayed by measuring superoxide production in intact cells. Typically, the measurement is conducted in the presence of a mitochondrial poison such as KCN, an inhibitor of NADH oxidase. Alternatively, the activity of the NADPH oxidase can be assayed in intact LacCer-responsive cells by measuring superoxide production The superoxide measurement can be performed in several ways including incubating the cells with a photosensitive polycyclic organic compound (e.g., an acridylium compound). Reduction of the polycyclic compound by superoxide causes light emission that can be detected by a standard photon counter. Preferred methods of measuring the NADPH oxidase activity are described in Bhunia, A. K. et al. (1997) *J. Biol. Chem.* 275:15642.

Additional in vitro assays are provided which measure one or more enzymes that have been found to be modulated by LacCer and GalT-2 inhibitor compounds disclosed herein. The enzymes include Ras-GTP-binding protein, Raf-1, mitogen activated protein (MAP) kinase (MEK-2), and other mitogen activated protein kinases such as p44 MAPK. Each of these enzymes can be assayed by one or a combination of conventional methods.

For example, incorporation of a nucleoside triphosphate, particularly a cyclic nucleoside triphosphate such as guanidine nucleoside triphosphate (GTP) into an oncogene protein such as the ras protein (i.e. ras-GTP loading) by the ras-GTP-binding protein can be measured by a number of distinct approaches including direct detection of nucleoside triphosphate (e.g., GTP) incorporation into Ras. For example, in one approach, LacCer-responsive cells are metabolically labeled with radioactive orthophosphate (e.g., $^{32}$P-labeled) to detectably-label the GTP inside the cells. The labeled cells are incubated with LacCer followed by a GalT-2 inhibitor compound and then washed and lysed in a suitable lysis buffer such as RIPA (see below). Subsequently, the cell lysate is separated on suitable TLC plates. The TLC plates are exposed to X-ray film and then subjected to densitometry, if desired, to quantitate incorporation of the GTP into the Ras protein. A preferred method for detecting ras-GTP loading has been disclosed in Chatterjee, S. et al., (1997) *Glycobiology*, 7:703.

Methods are also provided for measuring the activity of the Raf-1 and Mek-2 enzymes. For example, in one approach, the LacCer-responsive cells are incubated with LacCer and a potential GalT-2 inhibitor compound, washed, and then harvested after about 1 to 60 minutes, preferably 1 to 10 minutes or less, after exposure to the LacCer. Whole cell lysates are prepared and then subjected to standard SDS-PAGE gel electrophoresis. The gels are transferred to a suitable membrane support and then probed with and-RAF-1 or anti-MEK antibody in accordance with conventional Western blot hybridization procedures. Preferred examples of assays for measuring the Raf-1 and Mek-2 enzymes are disclosed in Bhunia, A. K. et al., (1996) *J. Biol. Chem.*, 271:10660.

Additional in vitro assays are provided which measure activity of DNA binding proteins, e.g., transcription factors such as c-fos, or the nuclear factor kB DNA binding protein (NF-kB). These DNA binding proteins have been surprisingly found to be modulated by LacCer and GalT-2 inhibitor compound. The DNA binding proteins can be assayed by a number of conventional approaches.

For example, the activity of the NF-kB DNA binding protein can be measured by a standard polyacrylamide gel mobility shift assay. The gel assay is performed after contacting LacCer-responsive cells with LacCer followed by a potential GalT-2 inhibitor compound. A cell lysate is prepared from the LacCer-responsive cells which is then contacted with an oligonucleotide sequence comprising (or consisting of) a recognized NF-kB DNA binding sequence. The reaction mixture is then incubated for a time sufficient to allow the NF-kB protein and the DNA binding sequence to form a specific binding complex. The specific binding complex is then separated on an SDS-PAGE polyacrylamide gel which is subsequently dried and exposed to X-ray film.

Additional in vitro suitable for measuring modulation by LacCer and GalT-2 inhibitor compounds include monitoring expression of cell proliferation factors. A preferred proliferating cell factor for such analysis is proliferating cell nuclear antigen (PCNA). In one suitable approach, the cultured cells are incubated with LacCer followed by a GalT-2 inhibitor compound and then washed with a suitable buffer. PCNA in the cultured cells can be detected (and quantified if desired) by using a monoclonal antibody that is capable of specifically binding the PCNA (e.g., PC10 antibody). See Sasaki, K., et al. (1993) *Cytometry* 14:876–882. The PCNA then can be detected in the cells by a variety of immunological methods including flow cytometery or imunohistochemical visualization of fixed cell sections.

All documents mentioned herein are incorporated by reference herein in their entirety.

The present invention is further illustrated by the following non-limiting examples.

General Comments

The following materials and methods (numbered 1–14 below) were used in Examples 1–16 below.

1. Isotopes and Chemicals. [$\gamma$-$^{32}$P] ATP were purchased from Amersham Life Science Inc. Glycosphingolipids and all other chemicals were purchased from Sigma Chemical Company, (St Louis, U.S.A). The purity of glycosphingolipids (>99%) was assessed by HPLC and or HPTLC. ICAM-1 antibody and SOD antibody were purchased from SantaCruz Biotechnology, CA. Cell Tracker dye green and cell Tracker dye orange were obtained Molecular Probes Inc., CA. DPI was from Calbiochem. USA 2. Cells. Hybridoma Eahy 926, derived from human umbilical vein endothelial cells (HUVEC; Clonetech) and human epithelial cell line AS49, was a kind gift from Dr. Roger Harrison (University of Bath, UK). These cells were cultured in plastic flasks in RPMI 1640 medium (Gibco BRL, Gaithersburg, Md.) containing 10% fetal calf serum, penicillin (100 U/ni) and streptomycin (0.1 mg/mL) (Gibco), passaged at confluence using 0.05% trypsin and 0.53 mmol/mL EDTA (Gibco), and then grown to confluence in 24 well plates.

Human blood was collected (in 10 U/mL heparin) from laboratory worker volunteers (by a protocol approved by the Johns Hopkins University Joint Committee for Clinical Investigation), and centrifuged at 1300 × g for 10 minutes. The white blood cell layer was removed and layered over cold Accu-prep gradient (Accurate Chemical and Scientific Corp., Westbury, N.Y.), and centrifuged at 600 × g for 30 minutes at 4° C. for leukocyte separation. The red blood cell (RBC)+PMN layer was resuspended in RBC lysing buffer (Sigma, St. Louis). After 20 minutes at room temperature, the preparation was centrifuged at 1300 × g for 2 minutes, and this step repeated until the PMN pellet was visibly free of RBCs. This suspension was consistently found to be comprised of greater than 95% PMNs by microscopic morphology following modified Wright-Giemsa staining (Diff-Quik Stain Set, Baxter, Miami Fla.).

3. Vehicle for Glycospingohpids. Stock solution of LacCer and other glycosphingolipids were prepared in DMSO and added to culture medium to achieve the desired concentrations of LacCer. Cells incubated with 0.01% DMSO served as a control. DPI stock solutions were prepared in DMSO and stored at −20° C. until use. Aqueous solutions of NAC or allopurinol were prepared either in medium or in buffer.

4. Measurement of Superoxide Production by Intact Eahy 926. Lucigenin, an acridylium compound (Sigma) that emits light on reduction and interaction with $O_2^-$ was used to measure $O_2^-$ production by chemiluminescence as described above. Confluently grown endothelial cells were harvested and $O_2^-$ was measured in intact endothelial cell suspension using a 96-well plate containing dark adapted lucigenin (500 $\mu$M) in balanced salt solution. The viability of the suspended cells as determined by trypan blue exclusion principle was >90%. LacCer was added to it as a stimulant and photon emission was measured every 20 seconds for 10mm in a scintillation counter (Packard TOP counter, USA). The GSL solutions (dissolved in DMSO) were added to cells to reach a final concentration of DMSO of 0.01%. Vehicle (0.01% DMSO) served as a control in most experiments. The amount of $O_2^-$ produced at each time point was calculated by comparison with a standard curve generated using xanthine oxidase.

5. Cell Fractionation and NADH/NADPH Oxidase Assay. Confluent endothelial cells were incubated with or without 5 $\mu$M LacCer. At different time intervals, cells were harvested, homogenized and membrane and cytosolic fractions were prepared as described above in example above NADH and NADPH oxidase activity was measured in both cytosolic and membrane fraction as described previously by lucigenin chemiluminescence method. In some experiments, NADPH oxidase activity was measured in the membrane preparations in the presence of 1 mM rotenone (a mitochondrial poison). Protein content was measured by the method of Lowry et. al. (*J. Biol. Chem.,* 193:265–275 (1951) with bovine serum albumin serving as a standard.

6. NF-kB DNA Binding Assay. Gel mobility shift assays of NF-kB DNA binding assays were performed as described (Yin et al. (1996)*J. Biol. Chem.,* 271:17974). Briefly, 20 $\mu$l reaction mixture contained 8–10 $\mu$g of nuclear protein plus a [$^{32}$P]-labeled oligonucleotide probe containing NF-kB binding site (5'-AGTTGAGGGGACITTCCCAGGC-3'SEQ ID No. 1) (Lenardo, M. J. and D. Baltimore (1989) *Cell,* 58:227) in binding buffer (10 mM Hepes, pH 7.5, 0.5 mM spermidine, 0.15 mM spermine, 5 mM EDIA, 10 mM dithiothreitol, 0.35 mM sucrose). The reaction mixture was incubated at room temperature for 15 minutes and loaded directly onto a 6.5% polyacrylamide gel in a buffer of 25 mM Tris borate (pH 8.0), 0.25 mM EDTA. In all experiments, proteins were separated by electrophoresis at 200 V for 2 hours at room temperature. Gels were dried and exposed to Kodak XAR film with intensifying screens. Assays were repeated with nuclear extracts obtained from three unique experiments and evaluated by phosphoimage analysis to ensure reproducibility of results.

7. ICAM-1 Expression Assay. A modified ELISA in 96well plates determined quantitative measurement of the expression of ICAM-1 on the surface of the endothelial cell monolayer. After the treatment of endothelial cell monolayers with or without LacCer, the cells were fixed with 3.7% formaldehyde (pH 7.4) containing 0.1 M Lysine monohydrochloride and 0.01 M sodium m-periodate for 20 minutes at 4° C. and then blocked with PBS containing 1% BSA and 0.1 M glycine overnight at 4° C. The fixed monolayer was then probed with mouse monoclonal anti-human ICAM-1 antibody for 1 hour at 37° C. Next it was incubated with peroxidase-conjugated anti-mouse IgG F(ab')$_2$ for 1 hour at 37° C. After washing, a developing substrate [0.2% $H_2O_2$, 0.4mg/ml o-phenylenediamine] was added for 5mm and the reaction was stopped with 2(N)$H_2SO_4$. The plates were read on a spectrophotometric plate reader at 520 nm (Wertheimer, S. J. et al. (1992)*J. Biol. Chem.,* 267:12030). ICAM-1 expression was assessed qualitatively by immunofluorescence staining using fluorescent isothiocyanate (FITC) -conjugated IgG after fixing with or without LacCer incubated cells with 3.7% formaldehyde.

8. Adenovirus Vector-Mediated Overexpression of SOD in Endothelial Cells. A replication incompetent adenovirus (ad-SOD) carrying the cDNA for human CuZn-superoxide dismutase (SOD) (Crawford, L. E. et al., *J. Biol. Chem.,* 271:26863) and a control virus (ad-βgal) without SOD gene but encoding only the *E. Coli* lac Z gene (Guzman, R. J et al. (1994) *PNAS* (USA), 91:10732) was amplified in 293 cells and purified as described (Crawford, L. E., supra). Confluently grown Eahy endothelial cells in 96-well plate (1.3×10$^4$ cells/well) were infected with virus containing CuZn-SOD gene in multiplicities of infection (MCI) ranging from 0 to 75. Another plate of endothelial cells were infected with control virus (ad-β-gal) of similar dilution. Twenty-four hours later, the cells were washed with PBS to remove uninfected virus particles. The endothelial cells were then incubated for an additional 48 hours in fresh medium. Next, the cells were fixed with 3.7% formaldehyde in PBS. The expression of intracellular SOD by the endothelial cells was measured by ELISA after permeabilization with 0.2% Triton X-100 in PBS for 20mm. The permeabilized endothelial cells were probed with monoclonal anti-human SOD antibody and then with FITC-conjugated goat anti-mouse IgG. FITC fluorescence was measured employing a fluorescence plate reader (CytoFluor 2300) at 480 nm (excitation) and 530 nm (emission). SOD activities in cell extracts were measured by the method of McCord and Fridovich (McCord, J. M. and I. Fridovich (1969) *J. Biol Chem.,* 244:6049).

9. Isolation and Confocal Microscopic Study of Adhesion of Human Neutrophil to Endothelial Cells. For the isolation of polymorphonuclear leukocytes (PMNs), human blood was collected in 10 U/ml heparin from laboratory volunteers. Blood was centrifuged at 1300 × g for 10 mm at 4° C. The white blood cell layer was removed and layered over cold Accu-prep gradient (Accurate Chemical and Scientific Corp., (Westbury, N.Y.), and centrifuged at 600 × g for 30 mm for the separation of leukocytes. The red blood cell (RBC)/PMN layer was resuspended in RBC lysing buffer (Sigma St. Louis). After incubation at room temperature the preparation was centrifuged at 1300 × g for 2 mm and this step was repeated until the PMN pellet was free of RBCs. The PMN pellet was then washed and resuspended in calcium-free phosphate buffered saline (PBS) (GIBCO). This suspension was found to contain >96% PMNs by microscopic morphology analysis following modified Wright-Giemsa Staining (Diff-Quick Stain Set, Baxter, Miami). The PMNs were labeled by incubation with 5 μM fluorescent Cell Tracker dye (green) for 30 minutes at 37° C. At the same time, LacCer stimulated (10 μM, 4 hours, 37° C. )/control (0.01% DMSO) endothelial cell monolayers grown in glass chamber slide were also labeled with 10 μM Cell Tracker dye (orange). These fluorescent labeled PMNs were incubated with confluently grown fluorescent-labeled endothelial cell monolayers in glass chamber slide for 30 minutes at 37° C. The non-adherent PMNs were removed by gentle washing with PBS. The slides were then treated with antifading reagent. A drop of 4% glycerol in PBS was added and a glass coverslip was mounted on the slide and photographed using fluorescence confocal microscopy.

10. Flowcytometric Analysis of the Expression of Adhesion Molecules on PMNs. Treated PMNs were rapidly cooled on ice, washed twice with cold washing buffer (PBS containing 0.1% BSA and 0.1% sodium azide), and then incubated with either monoclonal (m) anti-human (h) LFA-1 (CD11 a), m-anti-h Mac-1 (CD 11b), m-anti-h p150,95 (CD 11 c) or m-anti-h L-selectin (all from PharMingen., San Diego, Calif.), followed by FITC-conjugated m-anti-mouse IgG (American Qualex, San Clement, Calif.). The PMNs were gated by forward and side scattering for analysis by FACScan (Becton Dickinson, Cockeysville, Md.).

11. Measurement of ROM Generation by PMNs. 2',7'-dichlorofluorescein diacetate (DCFH-DA) (Molecular Probes, Eugene, OR) was used to determine the net cellular generation of ROMs by PMNs. $2 \times 10^5$ PMNs/well were incubated in 96 well-plates with/without various concentrations of N-acetylcysteine (NAC, a cell permeant, relatively nonselective antioxidant) (Sigma) or diphenyleneiodonium chloride (DPI, a NADPH oxidase inhibitor) (Sigma) for 20 minutes at 37° C., then DCFH-DA (final concentration 5 μmol/L). Graded concentrations of LacCer were then added, the cells incubated for 45 minutes at 37° C. and read on a fluorescence plate reader at EX 480 NM/EM 530 nm (CytoFluor 2300, Millipore, Bedford, Mass.).

12. PMN-Endothelial Adhesion Assay. PMNs were labeled fluorescently by incubation with 5 μmol/L Calcein-AM (Molecular Probes) in calcium-free PBS for 20 minutes at 37° C., washed and resuspended in Hanks' balanced salt solution (Gibco) containing 0.2% bovine serum albumin (BSA). These PMNs were then treated with LacCer (or vehicle, 0.05% DMSO), washed 3 times with PBS and then plated on the unstimulated ec monolayers, which had been grown to confluence in 24-well plates. The PMNs (600 μL of $2 \times 10^6$/mL/well) then were incubated with the ecs for 30 minutes at 37° C. Non-adherent PMNs were then removed by gentle washing 3 times with PBS. The residual adherent PMNs (and ecs) were then lysed using 4mmol/L Zwittergent Calbiochem, La Jolla, Calif.) and the plates read on a fluorescence plate reader (Millipore) at EX 480 nm/EM 530 nm. The number of adherent PMNs were expressed as number of PMN/mm² ec monolayer, based on the mean fluorescent intensity of each PMN, as determined from a standard curve.

13. Additional Methods. LacCer, ceramide and GicCer (all from Sigma) were prepared as described in examples below, and used as putative agonists for the stimulation of PMN adhesion molecule expression, assayed by FACScan. To explore the mechanism involved in LacCer upregulation of Mac-1 on PMNs, PMNs were incubated with the following specific inhibitors for 20 minutes at 37° C., and then stimulated with 100 nmol/L LacCer for 20 minutes: NAC (a cell permeable, relatively nonselective antioxidant); DPI (a neutrophil NADPH oxidase inhibitor); or BAPTA/AM (an intracellular calcium buffer) (Calbiochem) were used to determine whether ROMs, NADPH oxidase activity, or calcium fluxes mediate this Mac-1 upregulation, respectively. Genistein (Calbiochem), staurosporine (Calbiochem), or quinacrine dihydrochloride (ICN, Aurora, Ohio) was used for evaluating the possible involvement of tyrosine kinase, protein kinase C (PKC), or phospholipase $A_2$ (PLA$_2$), respectively, in LacCer-induced Mac-1 upregulation in hpMN. Finally, WEB 2086 (a specific PAF-receptor antagonist) (Boehringer Ingelheim, Ridgefield, Conn.) was used to determine the possible involvement of PAF, which is one of the metabolites metabolically downstream from PLA$_2$ which can upregulate PMN Mac-1. To rule out the possibility of adhesion stimulated by ec reactivity in some PMN adhesion assays, the ec monolayers in the half of each 24 well-plate were first fixed with 2% buffered formalin for 5 minutes and then washed 3 times with PBS. The ecs on the other half of the plate were left unfixed, but similarly washed before use for the adhesion assay. In the inhibition assay of PMN adhesion by quinacrine, PMNs were first incubated with increasing doses of quinacrine for 20 minutes, then stimulated with 100 nmol/L of LacCer for 20 minutes, followed by washing 3 times, and then plated onto formalin-prefixed ec monolayers in the presence of each concentration of quinacrine to eliminate a possible direct effect of quinacrine on the ecs. To evaluate the possible role of PMN CD11/CD18 in this adhesion response, PMNs were first incubated with LacCer for 20 minutes at 37° C., washed 3 times, incubated with m-anti-CD18 F(ab')$_2$ (mHm23, a generous gift from Dr. J. Hildreth, The Johns Hopkins University, Baltimore, Md.) for 15 minutes at 37° C., and then plated onto the ec monolayers without washing.

14. Statistical Analysis Values were expressed as means ±1 standard deviation. Apparent differences between normally distributed means were evaluated for significance by the Student's t-test. Apparent differences in dose-responses were evaluated by one-way analysis of variance. Values of $p<0.05$ were considered to indicate statistical significance.

Example 1—D-PDMP inhibits TNF-a Induced ICAM-1 Expression and GalT-2 Activity in Endothelial Cells TNF-α was found to exert a concentration-dependent stimulation of ICAM-1 expression, and 1.7-fold increase in GalT-2 activity (FIGS. 1A–C). Preincubation of endothelial cells with (1R, 2R)-1-phenyl-2-decanoylamino-3-morpholino-1-propanol (i.e. D-PDMP) effected a concentration-dependent decrease in ICAM-1 expression and GalT-2 activity induced by TNF-α. Moreover, the D-PDMP mediated inhibition of ICAM-1 expression by TNF-α was bypassed by the addition of exogenous LacCer (FIG. 1B). The results indicate that TNF-α stimulated GalT-2 activity. The LacCer produced can in turn stimulate ICAM-1 expression. This phenomenon can be abrogated by D-PDMP and bypassed by the addition of exogenous LacCer.

Example 2—Measurement of Glycosphinogolipid Levels and GalT-2 Activity in Rabbits Receiving D-PDMP Experiments were performed on rabbits to examine the effects of D-PDMP on aortic stenosis following balloon angioplasty. The rabbits were given intramuscular injection of D-PDMP (10 mg/kg) or vehicle 24 hours prior to balloon angioplasty and this regimen was continued for 15 days. Next, the thoracic aorta was harvested, the glycosphingolipids was measured by HPLC analysis, and GalT-2 activity was measured employing assays described above.

The level of GlcCer and LacCer was found to decrease significantly in rabbits receiving D-PDMP. Concomitantly, the activity of GalT-2 was also decreased ~1.7-fold (see Table 1 below). Thus, D-PDMP inhibited GalT-2 activity and decreased the level of LacCer in rabbit thoracic aorta. The results also indicate that rabbit balloon angioplasty is a feasible model to study in vivo effects of D-PDMP or other GalT-2 inhibitor compounds on stenosis.

TABLE 1

Effects of D-PDMP on the levels of glycolipids and GalT-2 activity in rabbit thoracic aorta.

| | GSL Concentration ($\mu$g/gm wet weight) | | GalT-2 Activity |
|---|---|---|---|
| | GlcCer | LacCer | (nmol/mg protein/2 hour) |
| Balloon Angioplasty + Vehicle | 10 | 14 | 1.03–0.25 |
| Balloon Angioplasty + D-PDMP | 6 | 10 | 0.62–±0.01 |

Example 3—Effects of D-PDMP on Intimal Proliferation Following Balloon Angioplasty in Rabbits Twenty-four hours prior to balloon angioplasty, rabbits were given intramuscular injections of vehicle alone or 10 mg D-PDMP/kg in vehicle. Daily injections of D-PDMP continued for six weeks after balloon angioplasty. Next, the rabbits were euthanized by $CO_2$ asphyxia and the aorta was surgically removed. The site of balloon angioplasty was marked and the tissue was fixed with 10% formalin in phosphate buffered saline. The samples were prepared for histologic examination and photographed with the use of a Roche digital imaging system.

Figure 2A:
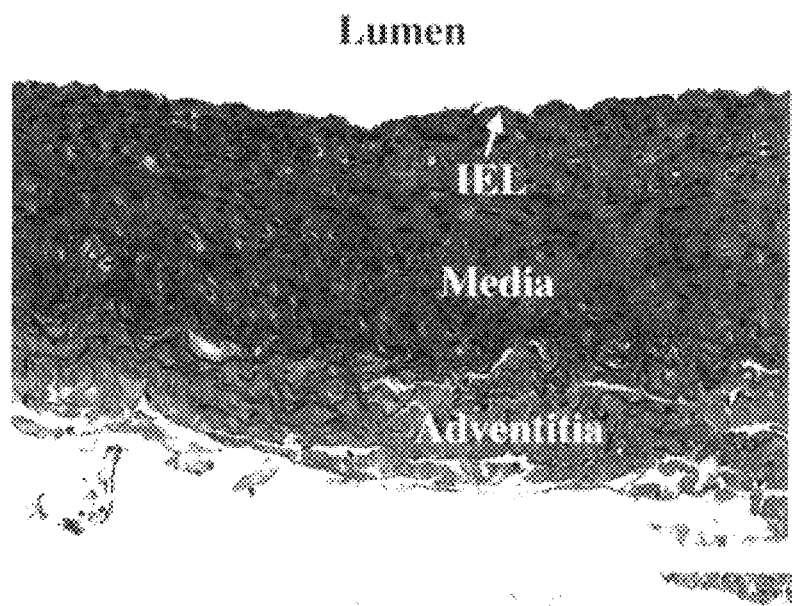
FIGS. 2A–C are photomicrographs of hematoxylin eosin-stained rabbit aorta sections following balloon angioplasty and treatment with D-PDMP.

FIG. 2A shows a section through the aorta of a control rabbit given D-PDMP for six weeks. Note that the endothelium, media and adventitia are clearly visible. Following balloon angioplasty and injection of vehicle alone (FIG. 2B), a marked intimal proliferation and expanded IEL characteristic of endothelial damage was observed. In sharp contrast (FIG. 2C), when rabbits were given injections of D-PDMP following balloon angioplasty, the endothelium had regenerated but some IEL expansion was still observed. The most remarkable finding was the complete absence of intimal proliferation at the site of balloon angioplasty of this rabbit. The data in Table 1, above demonstrates that D-PDMP can reduce the level of glucosylceramide and LacCer and decrease the activity of GalT-2 in the aorta of balloon angioplasty rabbits, compared to control.

Figure 2B:
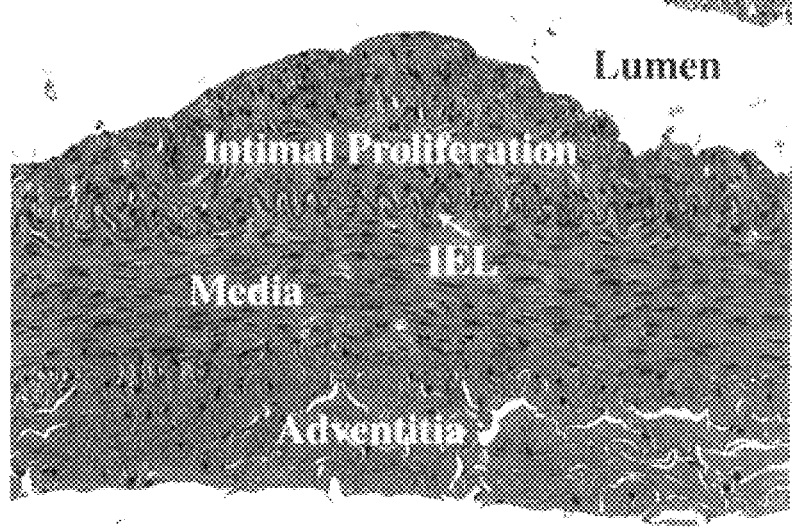
Figure 2C:
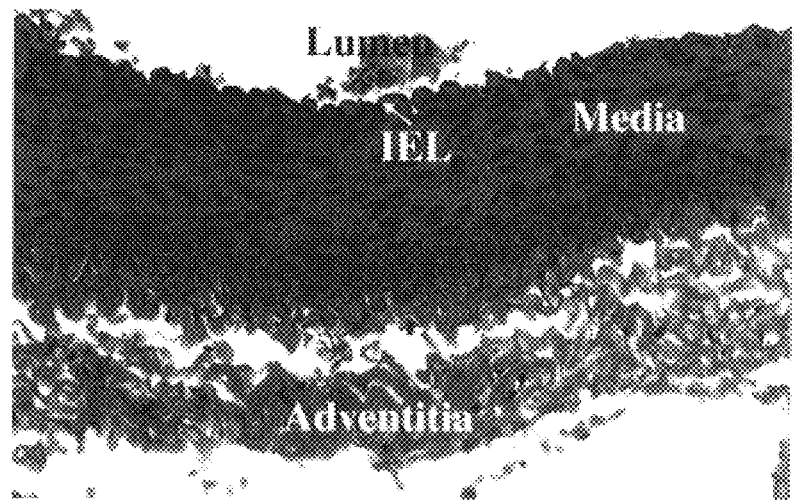

FIGS. 2A–C show photomicrographs of hematoxylin eosin-stained rabbit aorta sections following balloon angioplasty and treatment with D-PDMP, specifically: section of aorta from control rabbit (without balloon angioplasty) injected with D-PDMP is depicted in FIG. 2A; section of aorta from balloon angioplasty rabbit (without treatment of D-PDMP) is depicted in FIG. 2B; and section of aorta from balloon angioplasty rabbit treatment with D-PDMP is depicted in FIG. 2C.

Example 4—LacCer Induces Generation of Superoxide in Endothelial Cells LacCer stimulated the generation of $O_2^-$ in a concentration (FIG. 3A) and time (FIG. 3B) dependent manner in intact Eahy 926 cells, as measured by lucigenin chemiluminescence. Other GSLs and their constituents did not stimulate the generation of $O_2^-$ in Eahy 926 cells. The maximum generation of $O_2^-$-(2.7nmol/mni/mg protein) was observed at 5 $\mu$M concentration of LacCer after 5 minutes.

FIGS. 3A–B shows that LacCer stimulates superoxide generation in Eahy 926 cells. Confluently grown endothelial cell monolayers were harvested and suspended in balanced salt solution. Next, the generation of superoxide as measured by lucigenin chemiluminescence method as described above in the General Comments of the examples. FIG. 3A shows the effect of various concentrations of LacCer on the rate of generation of superoxide in endothelial cells. Control (vehicle 0.01% DMSO) (O); LacCer (●). FIG. 3B shows the effect of time of incubation with LacCer on the generation of superoxide. Control (vehicle 0.01% DMSO) (O); LacCer (●). FIG. 3C shows the effect of different glycospingolipids and its constituents (5 $\mu$M) as indicated on the rate of generation of superoxide after 2.5 min. incubation (control, empty box; treated, stippled box). Each point is the mean ± S.D. of five individual experiments.

Example 5—LacCer stimulated NADPH oxidase dependent $O_2^-$ Production in Eahy 926

Figure 4A:
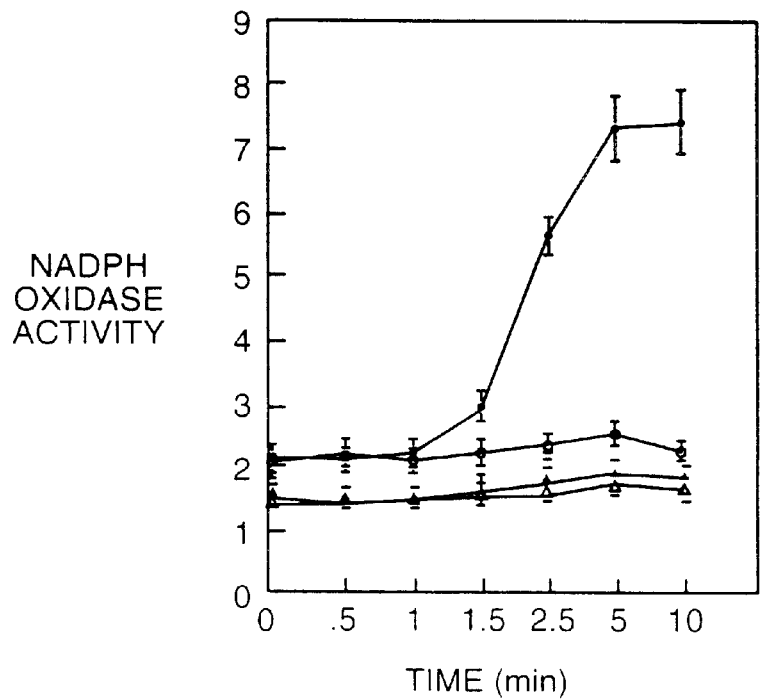
FIGS. 4A–B are graphs showing that LacCer stimulates activity of NADPH oxidase in Eahy 926 cells (a human endothelial cell line). Similar results have been obtained with a human umbilical cell line.
Figure 4B:
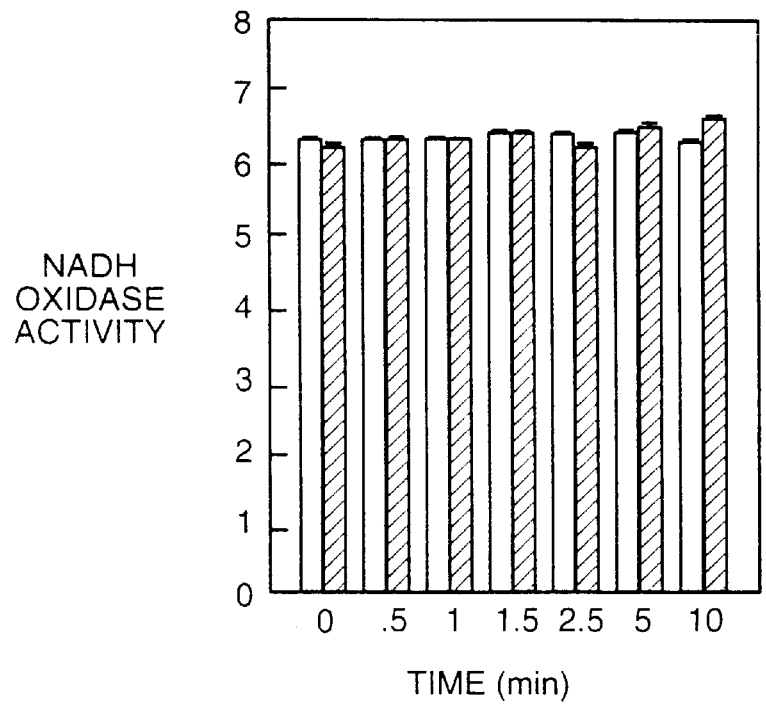

At various time points, following stimulation with or without LacCer, NADPH oxidase activity was measured in membrane preparations using NADPH as a co-factor. Stimulated NADPH dependent oxidase activity was observed in membrane preparations of LacCer treated Eahy 926 cells. At 5 minutes about 3-fold stimulation of NADPH oxidase activity was observed with 5 $\mu$M LacCer as compared to non-stimulated cells membrane preparations (FIG. 4A). Pre-incubation of LacCer stimulated/non-stimulated cells membrane preparations with DPI, a potent NADPH oxidase inhibitor (see examples above), attenuated the LacCer induced increase in NADPH-dependent oxidase activity in both the membrane preparations (FIG. 4A). In contrast NADH oxidase activity in LacCer stimulated/non stimulated membrane preparations remained unchanged (FIG. 4B). No NADPH oxidase or NADH oxidase activity was observed in LacCer incubated or without LacCer incubated cell cytosol. This data indicates that in endothelial cells LacCer induced $O_2^-$ production by specific activation of NADPH oxidase. On the other hand, allopurinol, a specific inhibitor for xanthine oxidase, failed to inhibit LacCer induced superoxide-generation. As rotenone incubated membrane did not inhibit NADPH oxidase activity, it is apparent that plasma membrane associated NADPH oxidase is involved in LacCer induced generation of $O_2^-$ in endothelial cells.

FIGS. 4A–B shows that LacCer stimulates the activity of NADPH oxidase in Eahy 926 cells. More specifically, FIG. 4A shows plasma membrane preparation of cells incubated with/without LacCer were used for the determination of NADPH oxidase activity as described in the general comments above. NADPH oxidase activity in control cells (O) and 5$\mu$ LacCer treated cells (●) and NADPH oxidase activity in control cells membrane after incubation with 10 $\mu$M DPI for 30 minutes (A) and in membranes from cells incubated with 10 $\mu$M DPI for 30 minutes +5 $\mu$M LacCer (shaded triangle). FIG. 4B shows NADH oxidase activity in membrane in control cells (clear blocks) and in cells incubated with LacCer (shaded blocks). No NADPH or NADH oxidase activity was observed in cytosol of ±LacCer incubated cells.

Example 6—LacCer induced NF-kB expression in Eahy cells

Figure 5A:
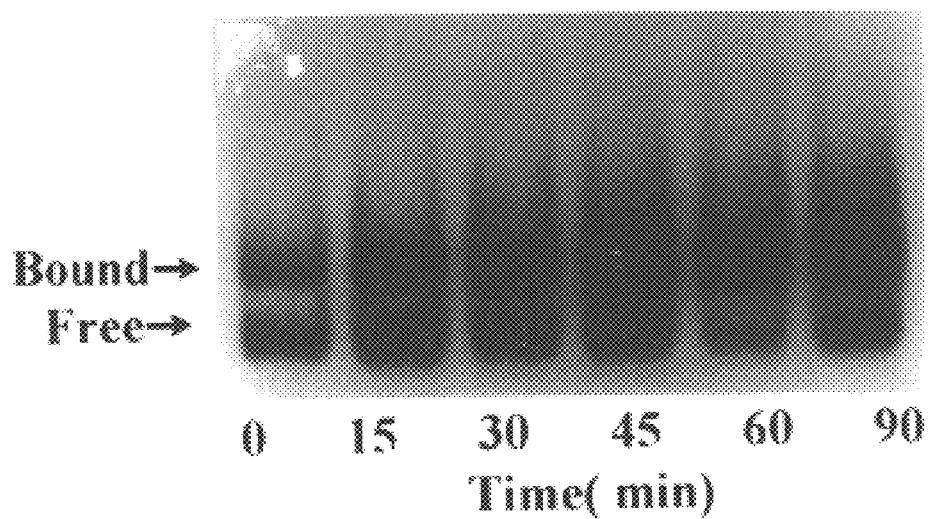
FIGS. 5A–B are representations of gel mobility assays illustrating effect of LacCer on the expression of NF-kB in Eahy 926 cells.
Figure 5B:
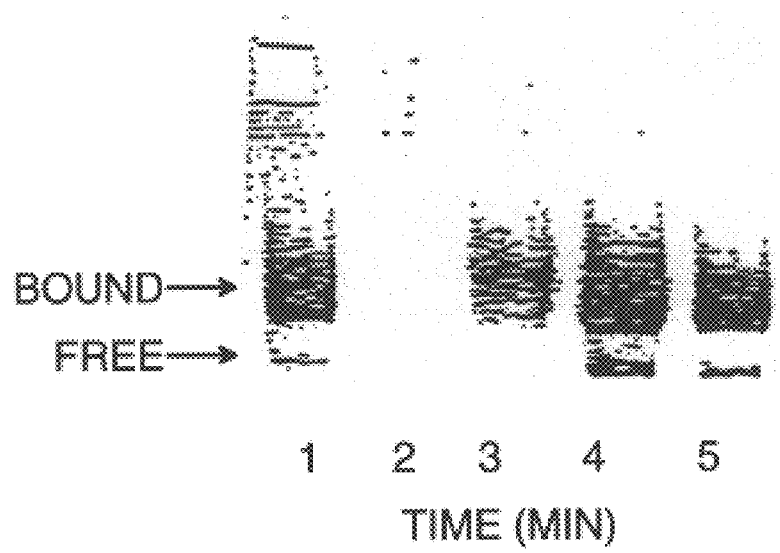

To ascertain whether the LacCer-induced signal for adhesion molecule expression might follow the NF-KB pathway, the nuclear concentration of NF-KB was measured in cells incubated with and without LacCer. Such gel mobility shift assays revealed that incubation of cells with 5 μM LacCer exerted a time dependent increase in the nuclear concentration of NF-kB (FIGS. 5A–B). Maximal expression of NF-kB was observed at 30 minutes after incubation with LacCer. These studies indicate that LacCer stimulated the expression of nuclear protein NF-kB in endothelial cells.

LacCer stimulated the binding activity of NF-kB to the consensus oligonucleotide sequence specific for NF-kB (SEQ ID NO.1). LacCer-induced generation of superoxide can induce expression of NF-KB.

FIGS. 5A–B illustrates effect of LacCer on the expression of NF-kB in Eahy cells. Cells incubated with 5 μM LacCer and different time intervals nuclear extracts were prepared as described below. Nuclear extracts (10 g of protein) were incubated with $^{32}$P-labeled NF-kB binding oligonucleotide probe in reaction mixture, reaction was stopped and run into 6% polyacrylamide gel. The gel was dried and autoradiographed.

Figure 6A:
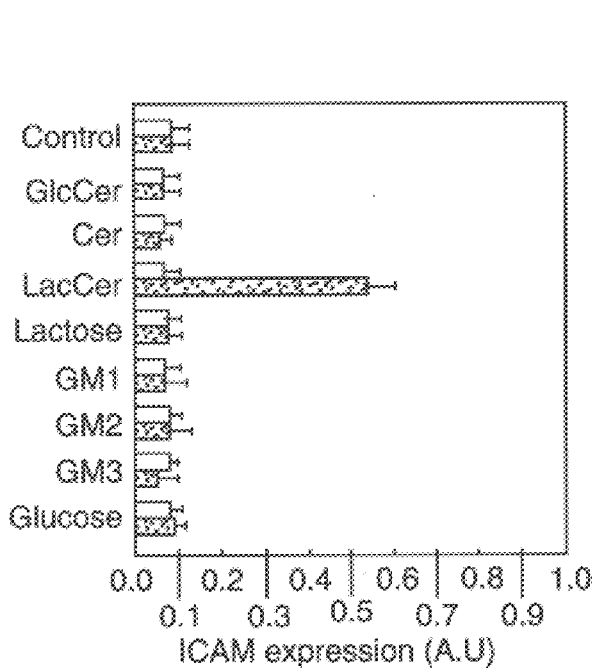
FIGS. 6 A–B are graphs showing effects of various glycosphingolipids on ICAM-1 expression in Eahy 926 cells.
FIGS. 6C–D are photographs showing effects of various glycosphingolipids on ICAM-1 expression in Eahy 926 cells.
Figure 6B:
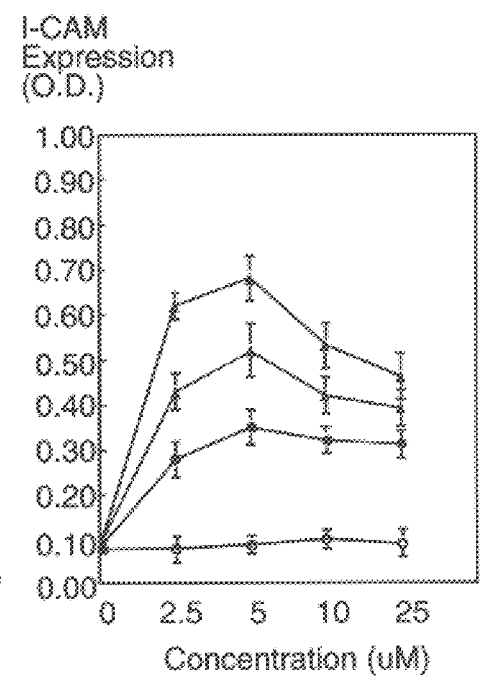
Figure 6C:
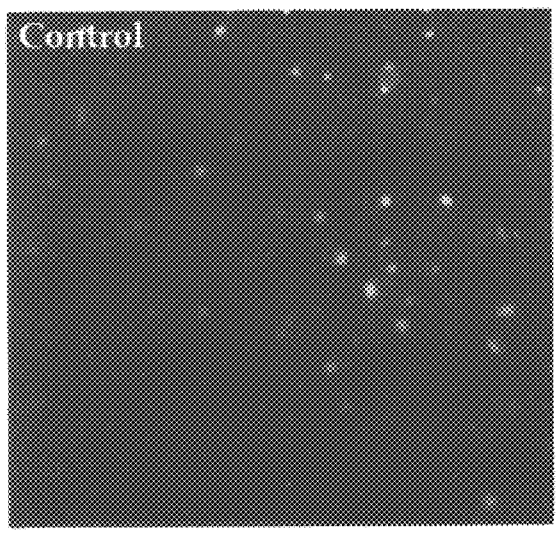
Figure 6D:
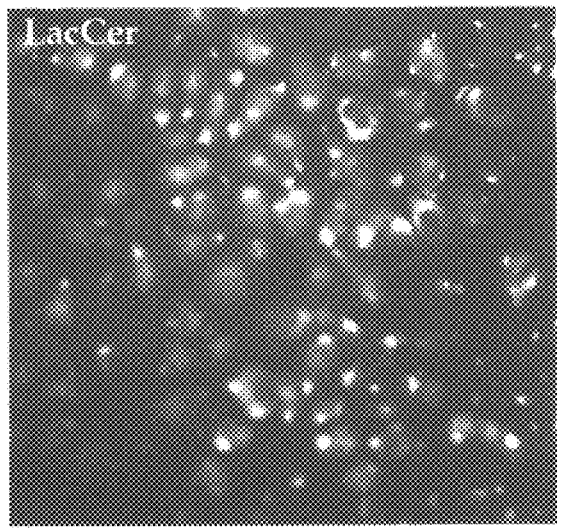

Example 7—LacCer Induced the ICAM-1 Expression in Endothelial Cells Intact Eahy 926 cells were incubated with various GSLs (10 μM) and their constituents. Only LacCer specifically stimulated the expression of intracellular cell adhesion molecule-1 (ICAM-1) (FIGS. 6A–B). Other GSLs and their constituents or gangliosides (GM 1, GM2, GM3, up to 50 μM) did not stimulate ICAM-1 expression (FIG. 6A). LacCer did not stimulate measurable expression of other adhesion molecules like VCAM-1 or P-selectin in Eahy 926. Immunofluorescence analysis, using ICAM-1 antibody followed by FITC conjugated anti-mouse 1 gG, confirmed the LacCer induced stimulation of cell surface ICAM-1 expression in intact endothelial cells (FIG. 6B) as compared to controls. Kinetic analysis revealed that LacCer induced ICAM-1 -expression in a time and concentration dependent manner (FIG. 6C). Maximal expression (7-fold as compared to control) of ICAM-1 was observed with 5 μM concentration of LacCer at 6 hours (FIG. 6D).

FIGS. 6A–C show effects of various glycosphingolipids on ICAM-1 expression in Eahy 926 cells. More specifically, FIG. 6A shows confluently grown Eahy 926 cells in 96-well plate (1×10$^4$ cells/well) were incubated with various glycosphingolipids (5 μM) for 4 hours. Next, cells were fixed with 3.7% formaldehyde in PBS and ICAM-1 expression was measured by modified ELISA assay using monoclonal ICAM-1 antibody as described in material and methods. Cells incubated with 0.01% DMSO served as a control and treatments ICAM-1 expression data was expressed optical density (O.D)/well. With respect to the results shown in FIG. 6B, endothelial cells were confluently grown in glass chamber slide and incubated with 5 μM LacCer for 4 hours. Next, cells were fixed in 3.7% formaldehyde and ICAM-1 expression was measured by immunofluorescence using ICAM-1 monoclonal antibody followed by incubation with FITC conjugated anti-mouse IgG and photographed employing fluorescence microscopy. FIG. 6B shows the effect of time and concentration of LacCer on ICAM-1 expression in endothelial cells. ICAM-1 expression was measured as described earlier. Cells incubated with 0.01% DMSO served as a control (O), LacCer incubated for 2 hours (●), LacCer incubated for 4 hours (Δ) and LacCer incubated for 6 hours (shaded triangle). Each point is the mean ±S.D. of five individual experiments.

Figure 7A:
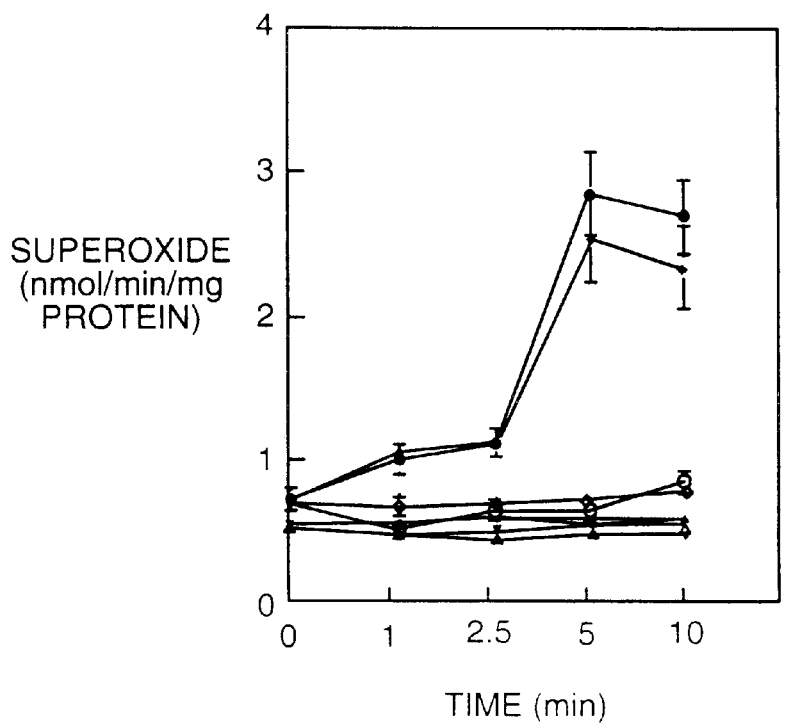
FIGS. 7A–B are graphs depicting effects of DPI, NAC and superoxide dismutase on LacCer-induced superoxide generation and ICAM-1 expression.

Example 8 Effect of NAC, DPI and Superoxide Dismutase (SOD) on LacCer Induced Superoxide Generation and ICAM-1 expression Cells incubated with 10 μM DPI for 30 minutes, failed to respond LacCer induced generation of $O_2^-$ (FIG. 7A). Similarly, cells incubated with an antioxidant, N-acetyl cysteine (NAC) (15mM) for 30 minutes, exhibited reduced LacCer induced endogenous levels of $O_2^-$- generation. However, exogenously added SOD did not inhibit the LacCer induced greater level of $O_2^-$ in endothelial cells (FIG. 7A). DPI or the antioxidants NAC or PDTC inhibited LacCer mediated stimulation of ICAM-1 expression (FIG. 7A). These findings suggest that the NADPH oxidase dependent generation of $O_2^-$ is involved in LacCer induced ICAM-1 expression.

Direct measurement by lucigenin chemiluminescence method revealed that LacCer stimulated $O_2^-$-generation in the endothelial cells in both time and concentration-dependent manner. LacCer induced level of $O_2^-$ was reduced by antioxidant NAC but not by exogenously added superoxide dismutase to cells indicating endogenous generation of $O_2^-$ (FIG. 7A). This observation may be due to the inability of SOD to penetrate the cell membrane but cell permeable NAC reduced the endogenous $O_2^-$level. LacCer induced $O_2^-$ endogenously not only in endothelial cells but also induced in smooth muscle cells and in neutrophils. See examples above.

Figure 7B:
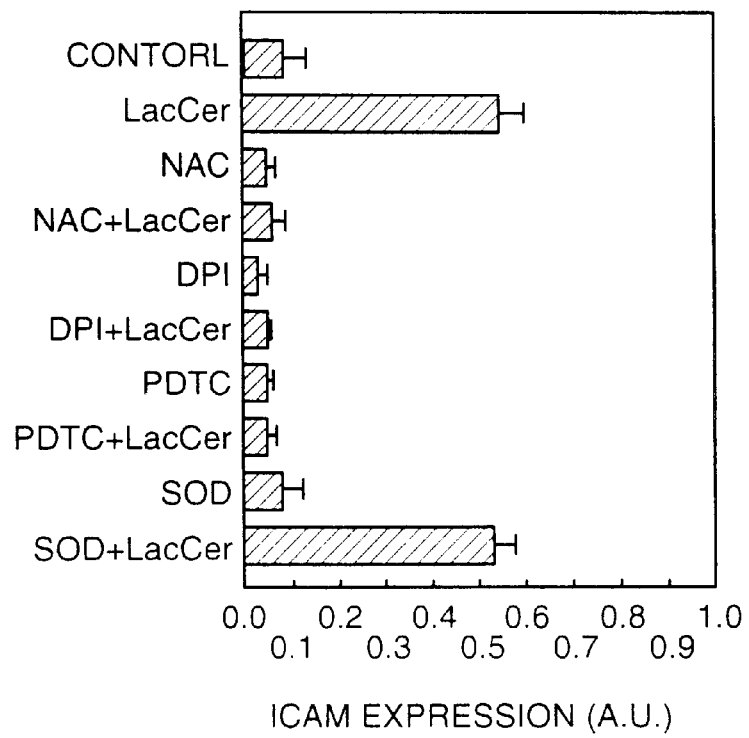

FIGS. 7A–B show effects of DPI, NAC and superoxide dismutase on LacCer induced superoxide generation and ICAM-1 expression. FIG. 7A shows the results of superoxide measured in cells incubated without (O) or with (●) LacCer (5 μM) and with 15 mM NAC (Δ), cells preincubated with 15 mM NAC +5 μM LacCer (▲), cells preincubated with 10 μM DPI (▽), cells preincubated with 10 μM DPI for 30 minutes followed by 5 μM LacCer (▽), incubation 200 U/ml SOD (◇), 200 u/ml SOD+5 μM LacCer (♦). FIG. 7B shows the results of ICAM-1 expression in cells incubated with 10 μM DPI for 30 minutes, 10 μM DPI for 30 minutes +5 μM LacCer for 4 hours, preincubated with 15 mM NAC for 30 minutes, preincubated with 15 mM NAC for 30 minutes +5 μM LacCer for 4 hours, 100 μM PDTC for 1 hours, 100 μM PDTC for 1 hours +5 μM LacCer for 4 hours.

Figure 8C:
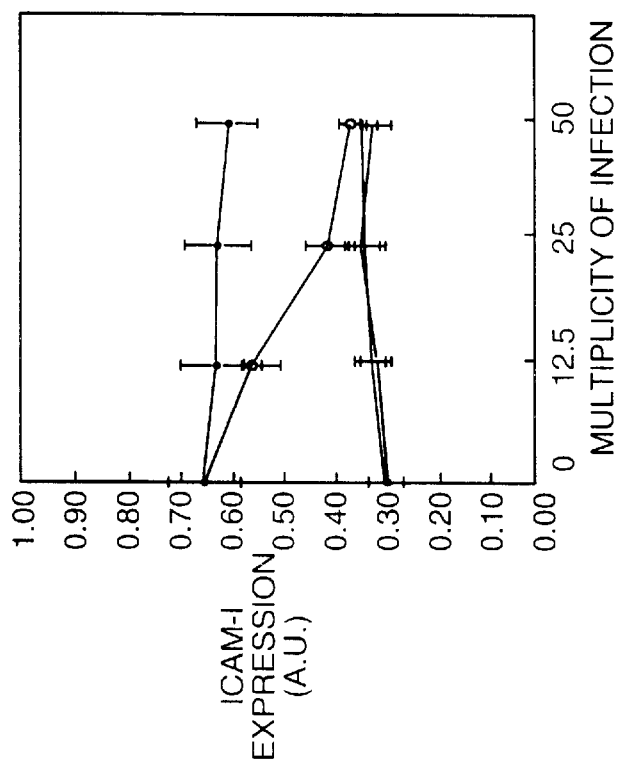
FIGS. 8A–C are graphs showing adenovirus-mediated overexpression of superoxide dismutase and ICAM-1 expression by LacCer in Eahy 926 cells.
Figure 8A:
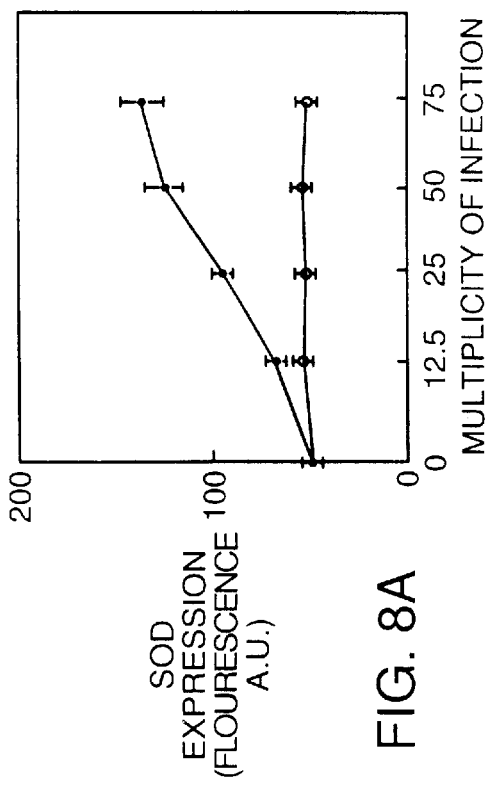
Figure 8B:
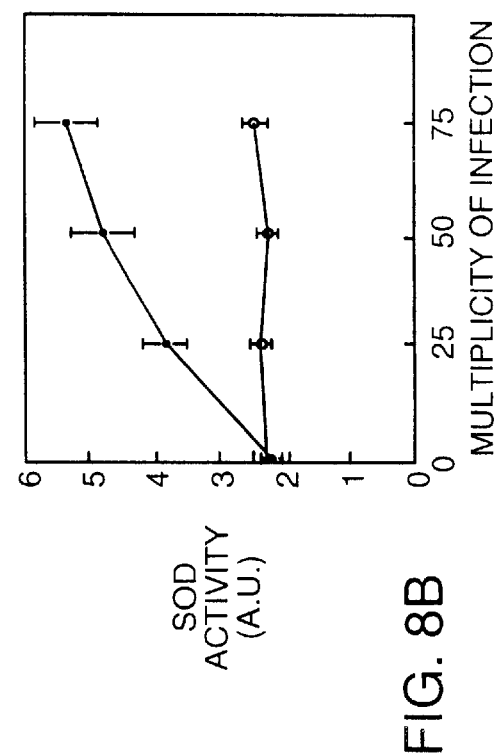
Figure 9A:
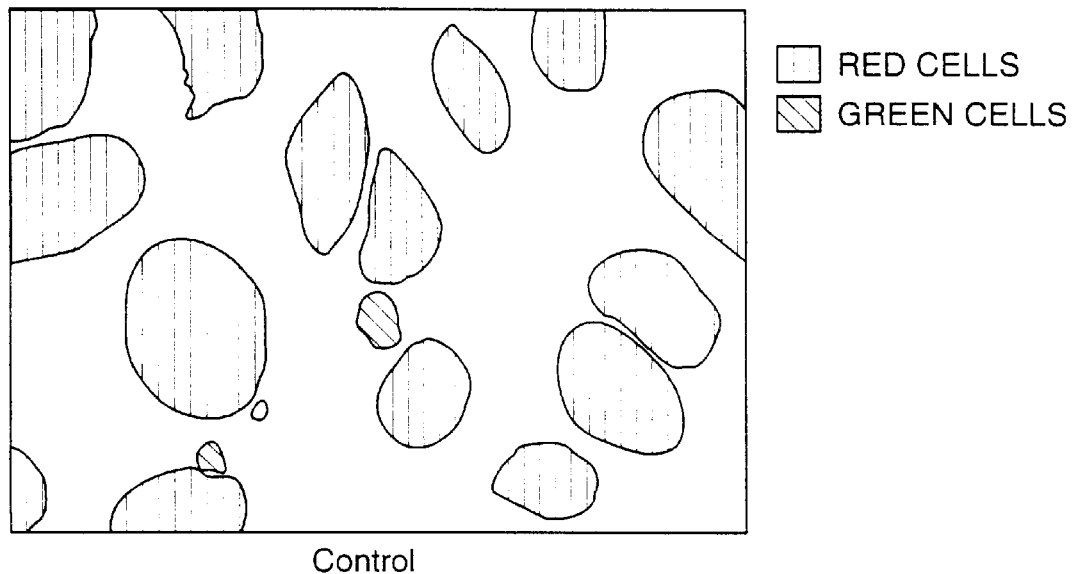
FIGS. 9A–D are drawings of color photographs (color indicated by shading) showing that LacCer stimulates neutrophil adhesion to Eahy 926 cells and NAC and DPI abrogate that phenomenon.
Figure 9B:
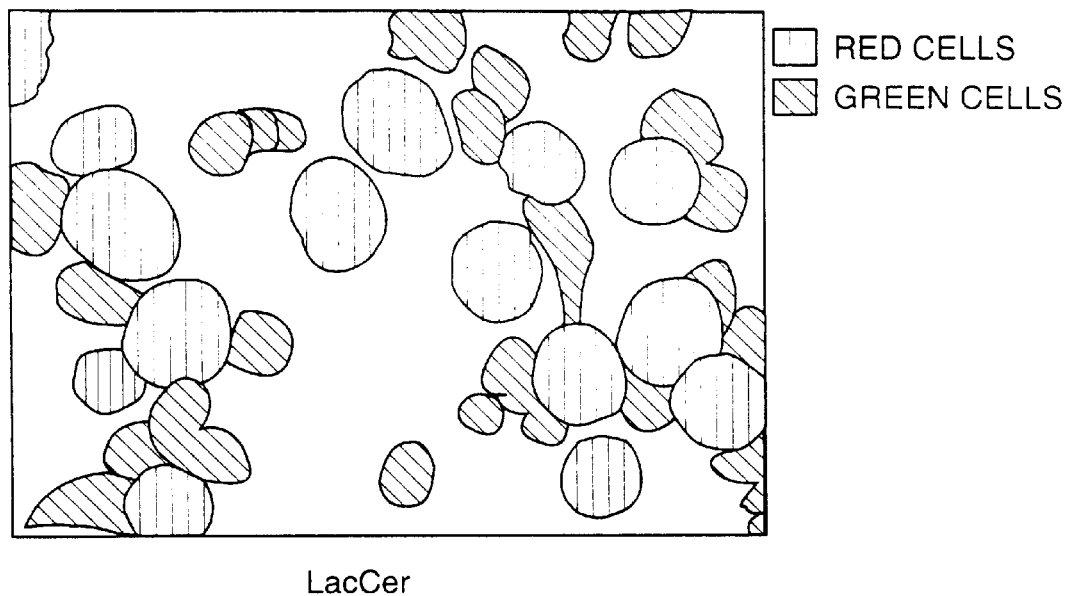
Figure 9C:
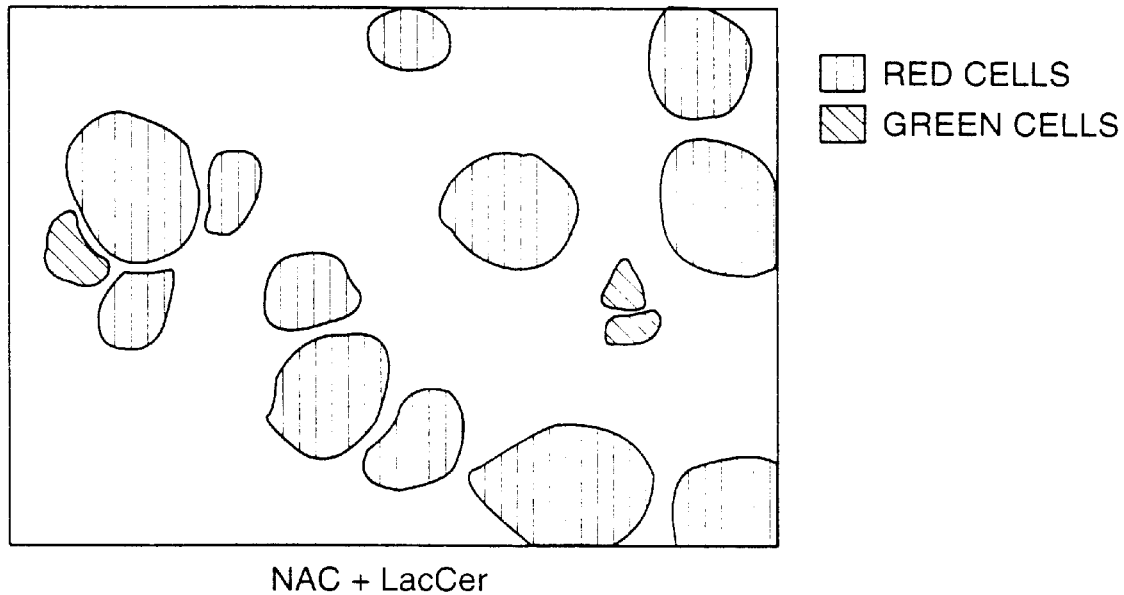
Figure 9D:
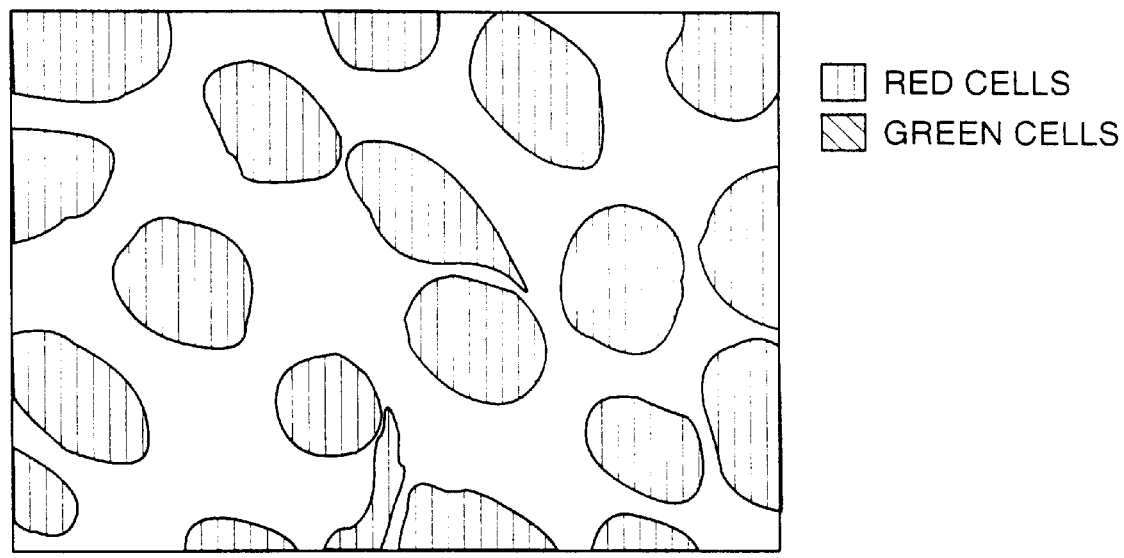

Example 9—Overexpression of Intracellular SOD inhibited LacCer-induced ICAM-1 Expression in Eahy 926 cells The expression of SOD in adenovirus (Ad) Ad-SOD infected endothelial was 2.5 fold higher at 50 MOI as compared to Ad-β-gal infected cells at the corresponding MOIs, as measured by the immunofluorescence using monoclonal anti-SOD (FIG. 8A). SOD activity in the Ad-SOD infected endothelial cell lysate was also increased with the increases of MOI (FIG. 8B). SOD enzymatic activity in Ad-SOD infected endothelial cells was also increased, dose-dependently, compared to that of the control cells (FIG. 8B). In the control cells LacCer stimulated ICAM-1 expression (FIG. 8C). However, as the level of intracellular SOD increased with the increase in MOI in the ad-SOD infected cells, LacCer induced ICAM-1 expression was proportionally inhibited. The adhesion of neutrophil to endothelial cells was also inhibited in the SOD overexpressed endothelial cells. This finding indicates that the LacCer induced stimulation of ICAM-1 expression and subsequent neutrophil adhesion was mediated by the production of $O_2^-$ intracellularly.

FIGS. 8A–C show adenovirus mediated overexpression of superoxide dismutase and ICAM-1 expression by LacCer in Eahy 926 cells. Overexpression of CuZn-SOD was performed in endothelial cells by adenovirus mediated CuZn-SOD gene transfer as described below. FIG. 8A shows the results of measurement of SOD expression in endothelial cells by immunofluorescence using monoclonal SOD antibody and FITC-labeled antimouse IgG after fixing cells with 3.7% formaldehyde and permeabilized with 0.2% Triton X-100 in PBS. Control virus (β-gal gene only) ( ) and Ad-SOD virus (■) infected cells lysate. FIG. 8B shows the results of SOD activity assay in cell lysates of SOD virus ( ) and control virus containing β-gal gene (shaded square) infected cells. FIG. 8C shows the results of immunofluorescence assay of ICAM-1 expression in endothelial cells in control virus infected cells (O), control virus infected cells +5 μM LacCer for 4 hours (●), Ad-SOD virus infected cells (Δ) and Ad-SOD virus infected cells +5 μM LacCer for 4 hours (▼). The data represents mean ± SD of two different experiments.

Example 10—Stimulation of Adhesion of Neutrophils to Eahy 926 by LacCer

In control endothelial cells, which were incubated with vehicle only (0.01% DMSO), neutrophil adhesion was not observed. In contrast, LacCer (5 μM markedly stimulated the adhesion of neutrophils (green fluorescent stained) to the endothelial cell monolayer (orange fluorescent stained) as examined under confocal fluorescence microscopy (FIGS. 9A–D). Endothelial cells preincubated with the antioxidants NAC or DPI attenuated LacCer-induced neutrophil adhesion (FIGS. 9A–D), suggesting a role for NADPH oxidase dependent $O_2^-$ generation in neutrophil adhesion via ICAM-1 expression.

FIGS. 9A–D show that LacCer stimulates neutrophil adhesion to Eahy 926 cells. Endothelial cells were confluently grown in glass chamber slides. Then cells were stimulated with 5 μM LacCer for 4 hours followed by fluorescent (orange color) labeling with cell tracker dye. Neutrophil stained green with a fluorescence probe were coincubated with the endothelial cells for 20 minutes and subjected to confocal microscopy as described below. In some experiments endothelial cells were incubated with either 10 μM DPI or 15 mM NAC for 30 minutes prior to incubation with 5 μm LacCer for 4 hours.

Example 11—LacCer Upregulated Mac-1 on PMNs

Figure 10A:
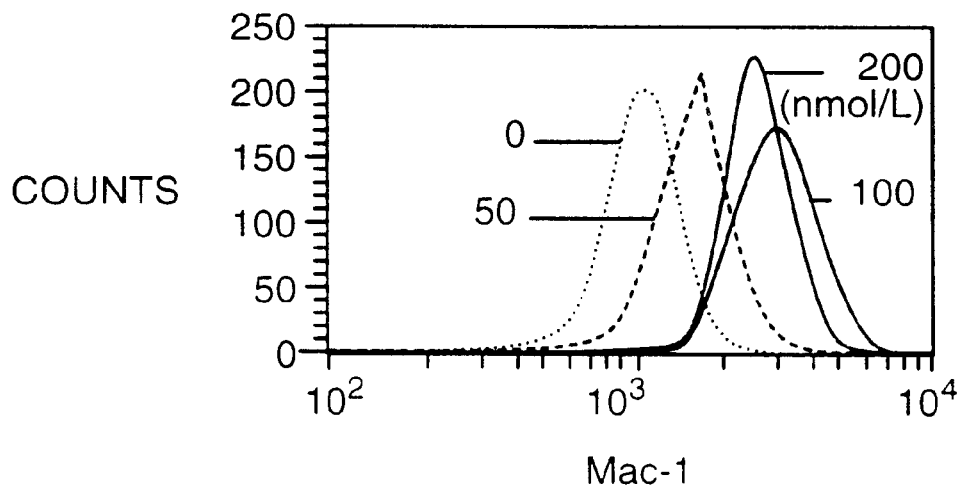
FIGS. 10A–L are graphs showing LacCer upregulation of Mac-1 expression in human PMNs.
Figure 10B:
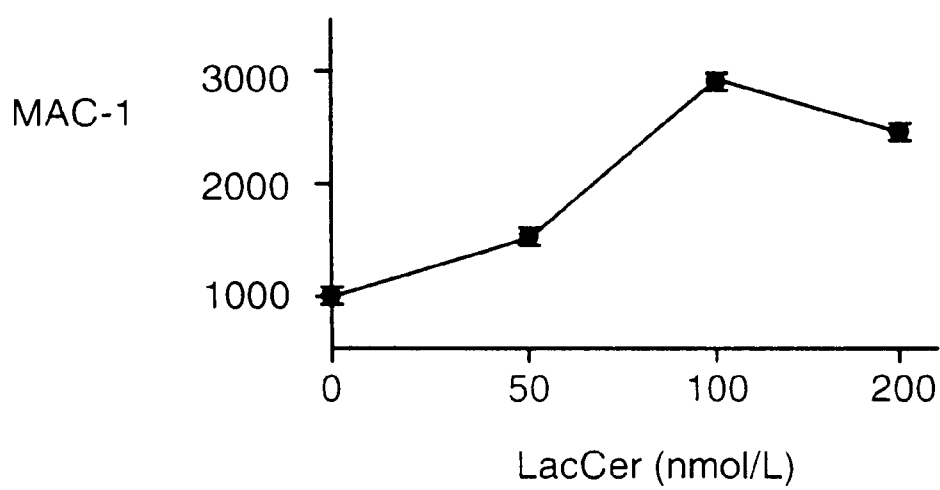
Figure 10C:
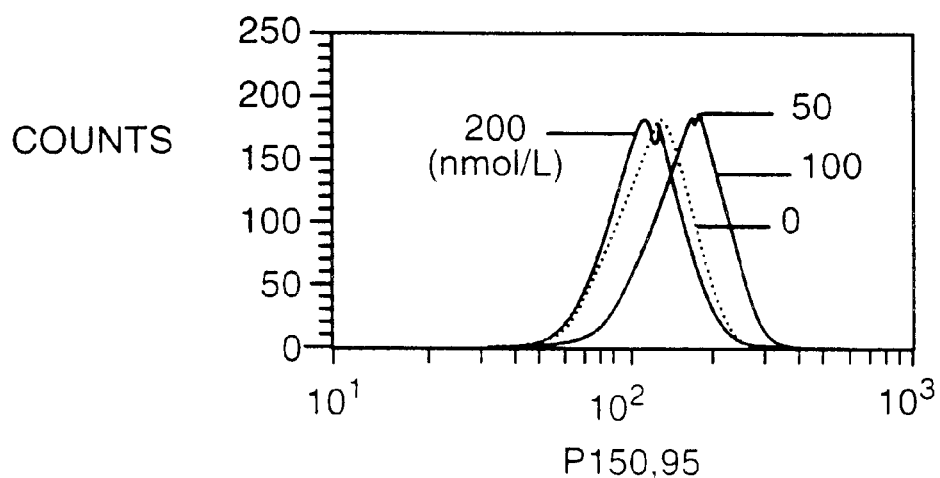
Figure 10D:
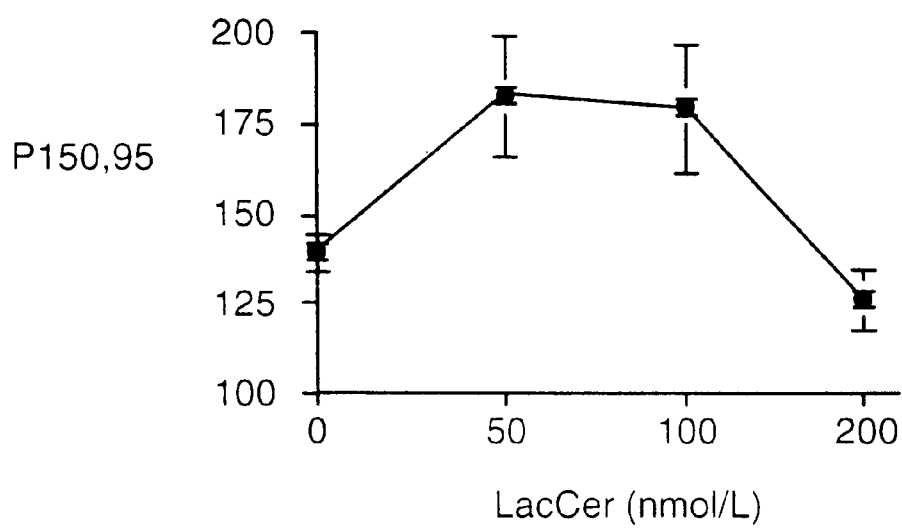
Figure 10E:
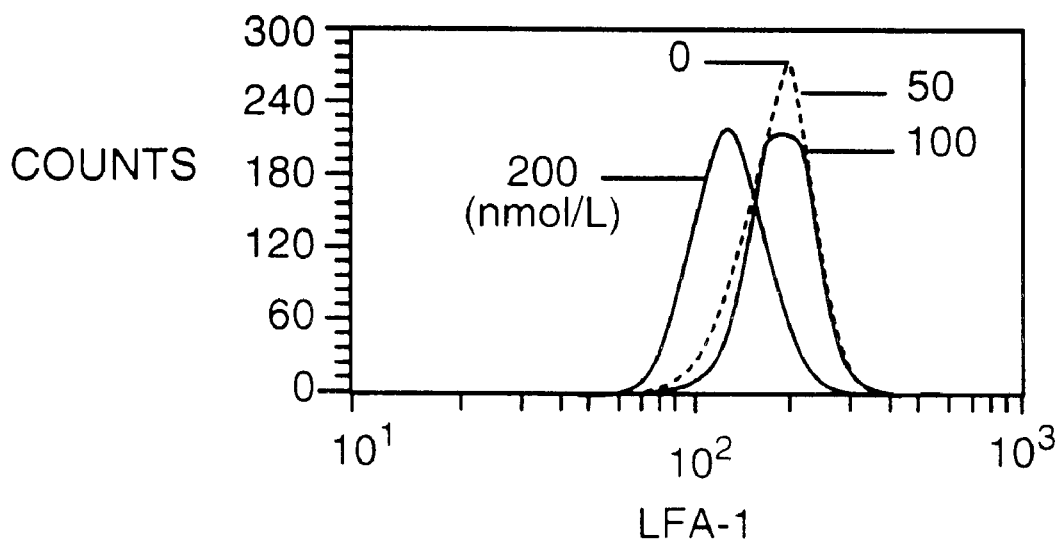
Figure 10F:
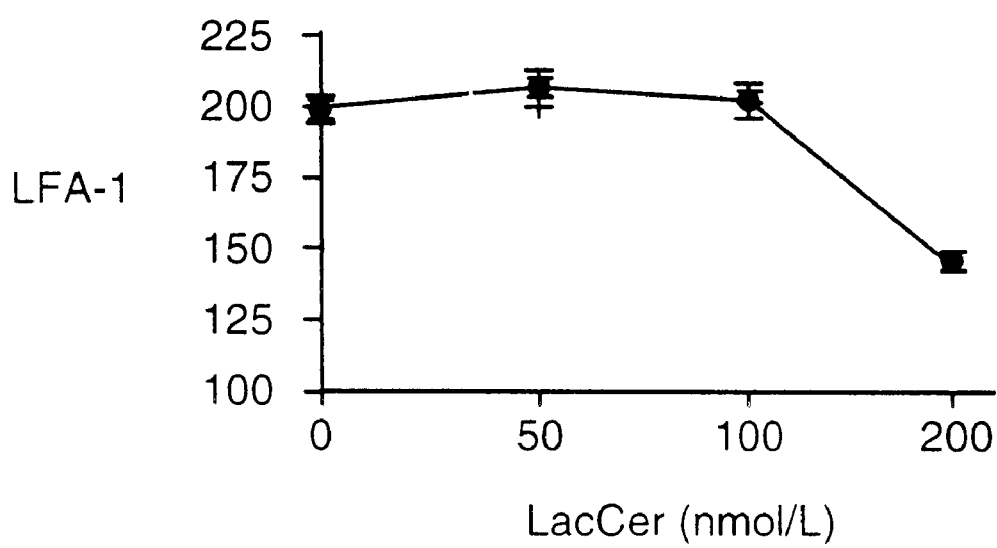
Figure 10G:
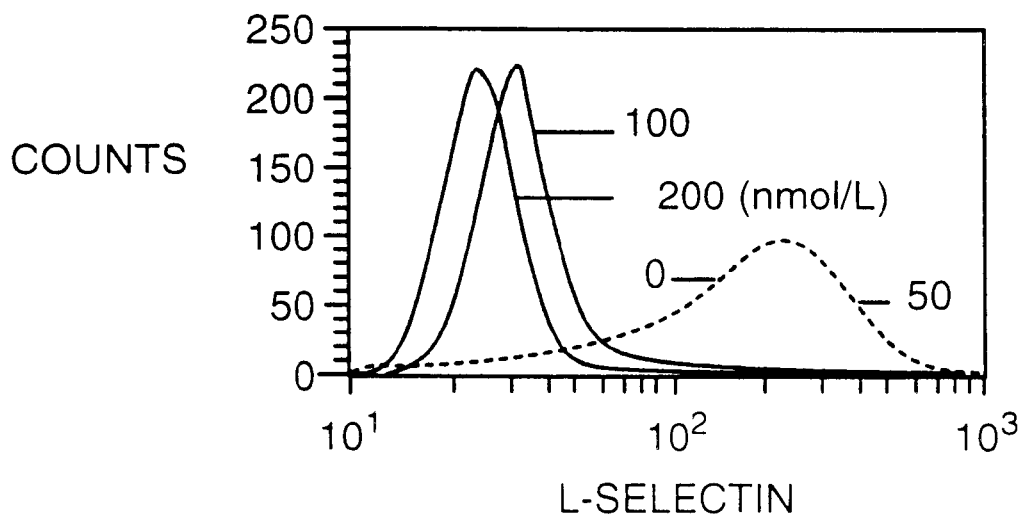
Figure 10H:
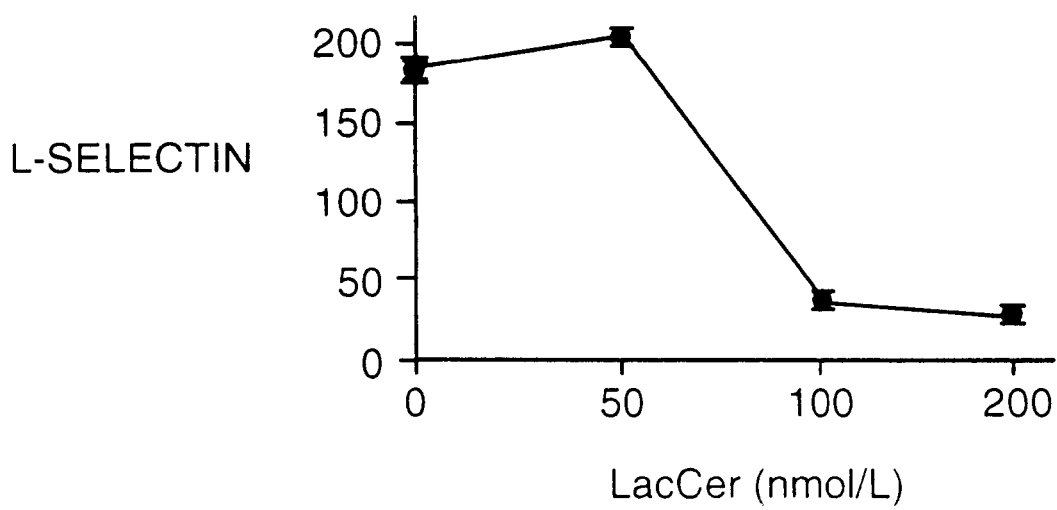
Figure 10I:
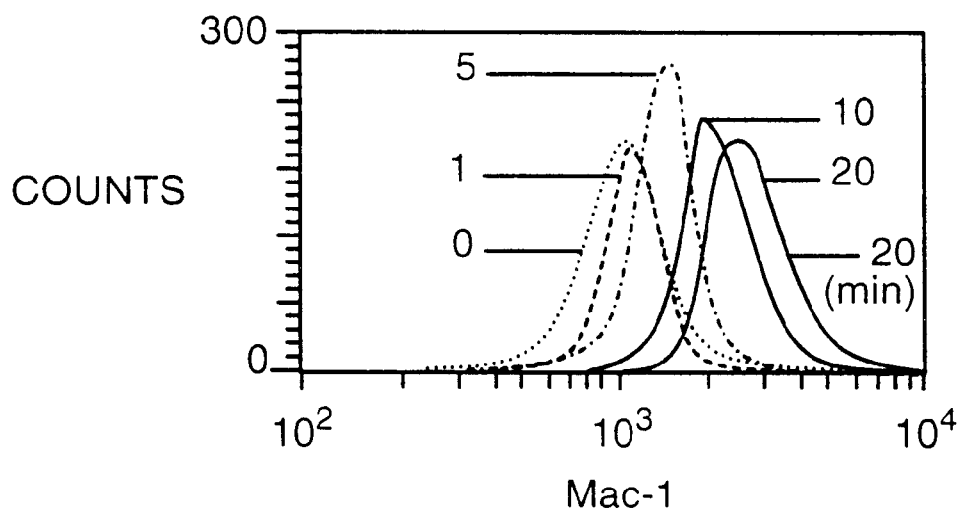
Figure 10J:
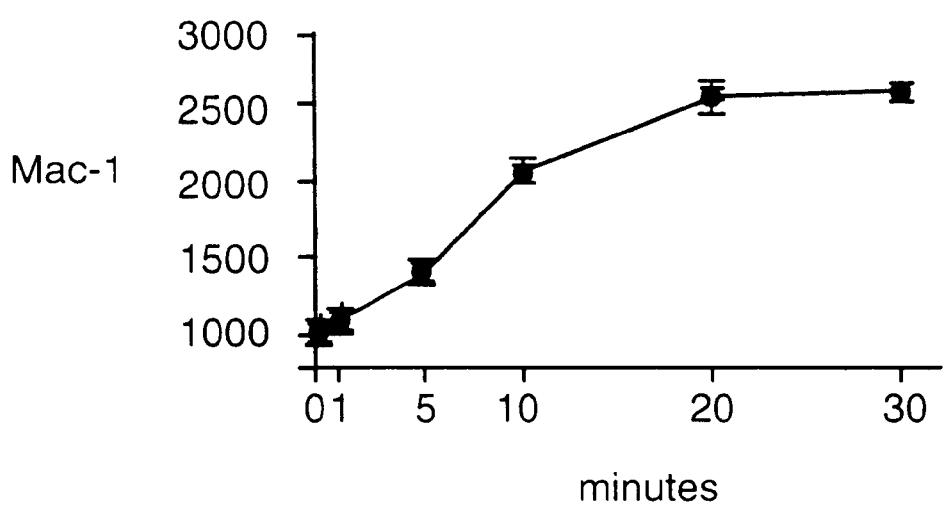
Figure 10K:
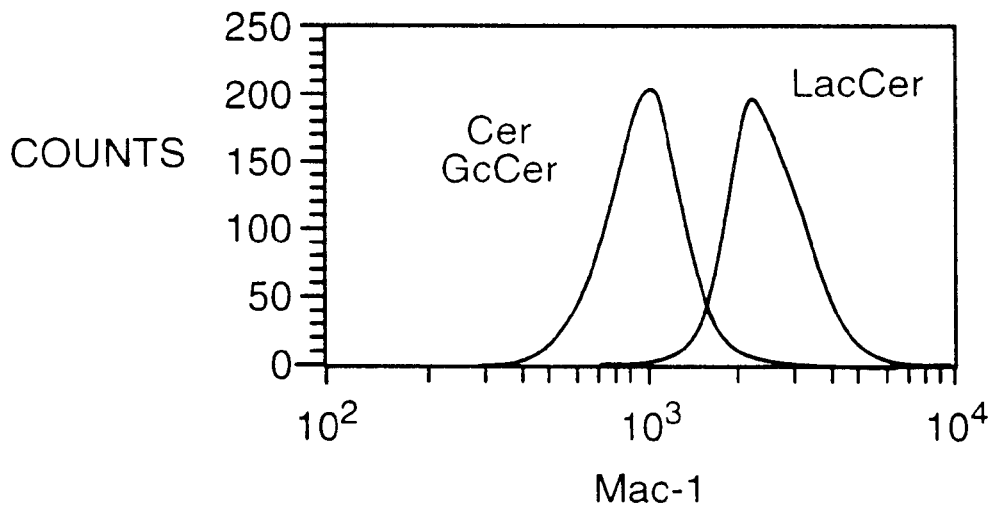
Figure 10L:
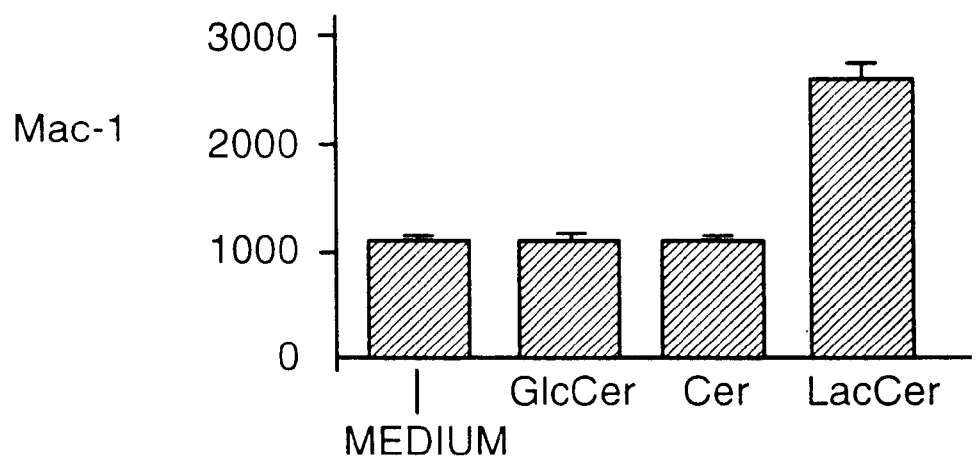

Treatment of PMNs with LacCer for 20 minutes upregulated CD11b/CD18 (Mac-1) in a dose-dependent fashion. Maximum stimulation of Mac-I expression in hPMNs was observed with 100 nmo/L LacCer (FIG. 10A). Similarly, LacCer (50–100 nmol/L) increased the level of CD 11/CD 18 (p150,95), but decreased the level at a higher concentration (200 nmol/L) at this time point. In contrast, LacCer did not change the levels of CD11a/CD18 (LFA-1) and L-selectin at lower concentrations, but downregulated both of them at higher concentrations (FIGS. 10C–D). Mac-1 was upregulated time-dependently by 100 nmol/L LacCer (FIGS. 10E) and maximum stimulation of Mac-1 level (2.5 fold compared to control) was observed 20 minutes after LacCer stimulation. On the other hand, other GSL, GlcCer or ceramide (100 nmol/L) did not alter Mac-1 expression on PMNs, indicating that this Mac-1 upregulation was a response specifically to LacCer (FIGS. 10 K, L).

Specifically, FIGS. 10A–D show results of the following protocol. PMNs were incubated with increasing concentrations of LacCer for 20 minutes, cooled rapidly on ice, washed and then incubated with either of monoclonal (m) anti-human (h) LFA-1, M-anti-h-MAC-1, m-anti-h p150,95 or m-anti-h L-selectin, followed by FITC-conjugated m-anti-mouse IgG. The PMNs were gated by forward and side scattering and analyzed using FACscan. E:PMNs were incubated with 100 nmol/L LacCer for indicated times and analyzed for Mac-1 expression. F:PMNs were incubated with 100 nmol/L LacCer, GlcCer, or ceramide (Cer) for 20 minutes and analyzed for Mac-1 expression. Data are means ± SD (n=3), based on the mean fluorescence of 15000 cells. LacCer upregulated Mac-1 and p150,95, but downregulated LFA-1 and L-selectin. GlcCer or ceramide did not alter Mac-1 expression.

Figure 11A:
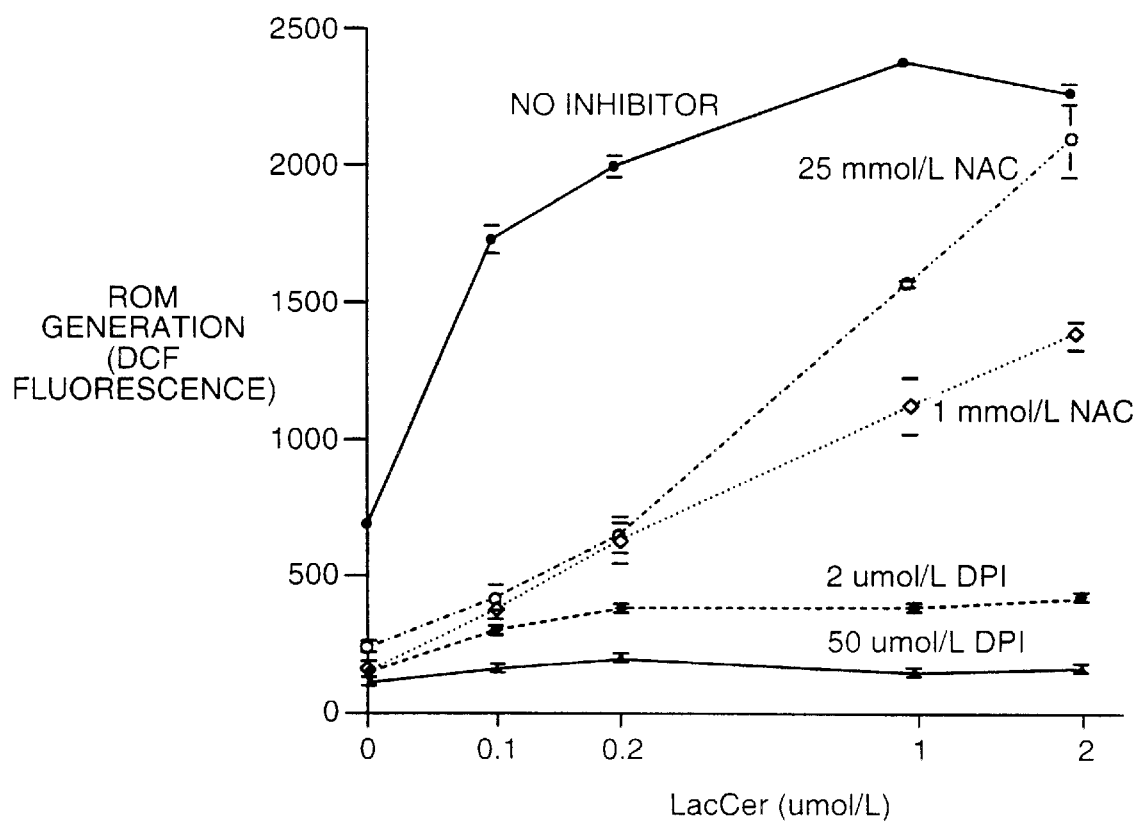
FIGS. 11A–B are graphs illustrating PMN ROM generation under various incubation conditions.

Example 12—LacCer Stimulated PMNs Generate ROMs via NADPH Oxidase As shown in the Examples above, LacCer activated superoxide generation via NADPH oxidase in human aortic smooth muscle cells, resulting in their proliferation. ROM stimulation by LacCer in PMNs, using DCFH-DA was also evaluated. A strikingly similar, positive, dose-dependent response was seen in these PMNs (FIG. 11A). This neutrophil ROM generation induced by 100 or 200 nmol/L LacCer (which had been sufficient to upregulate Mac-1 on PMNs), was inhibited by the antioxidant, NAC and completely blocked by the NADPH oxidase inhibitor, DPI (FIG. 11A).

In FIG. 11, PMNs were first incubated in 96 well-plates with or without N-acetylcysteine SAC) or diphenyleneiodonium (DPI) for 20 minutes at 37° C., then 2', 7'-dichlorofluorescin diacetate and various concentrations of LacCer were added. This plate was incubated for 45 minutes at 37° C. and read on a fluorescence plate reader. Data are means ± SD for 6 wells. Each data point with inhibitor is significantly different from the point without inhibitor at the same concentration of LacCer (p <0.001, *p <0.01 by Student's t-test). LacCer enhanced ROM generation by PMN, and NAC or DPI inhibited this additional ROM generation.

Figure 11B:
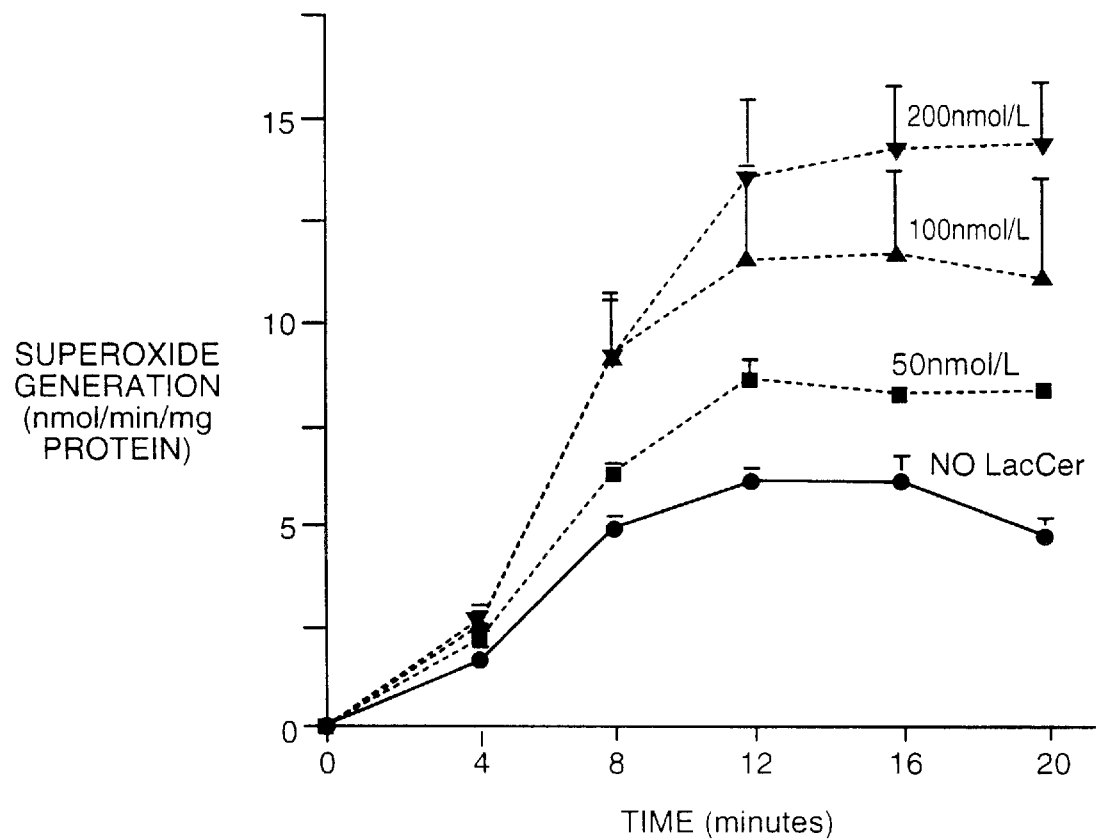

In FIG. 11B, PMNs were incubated with increasing concentrations of LacCer at 34° C., and lucigenin chemiluminescence was monitored for 20 minutes. Data are means ± SD from three individual experiments. *p<0.01 vs. no LacCer by ANOVA. LacCer enhanced this superoxide generation in a dose- and time-dependent manner.

Figure 12A:
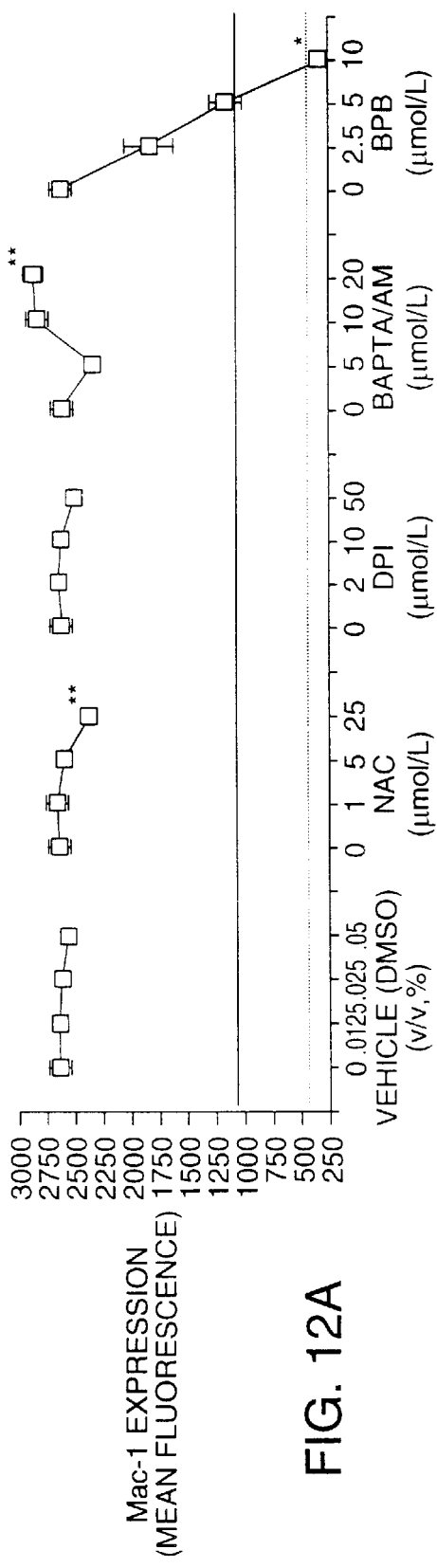
FIGS. 12A–B are graphs showing that phospholipase $A_2$ inhibition reduced LacCer upregulation of Mac-1 on PMN.
Figure 12B:
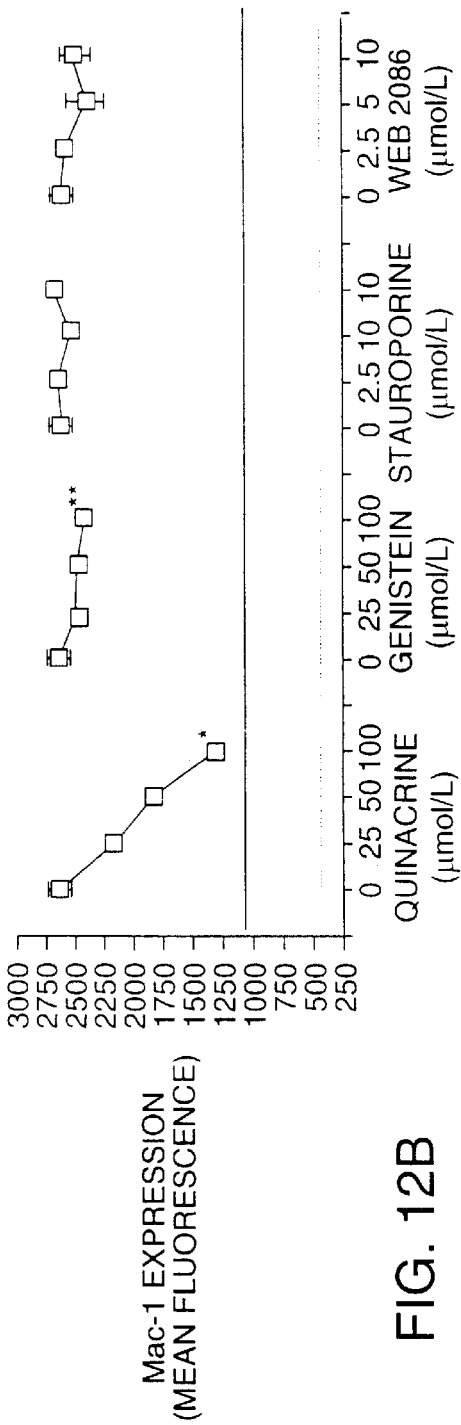
Figure 12C:
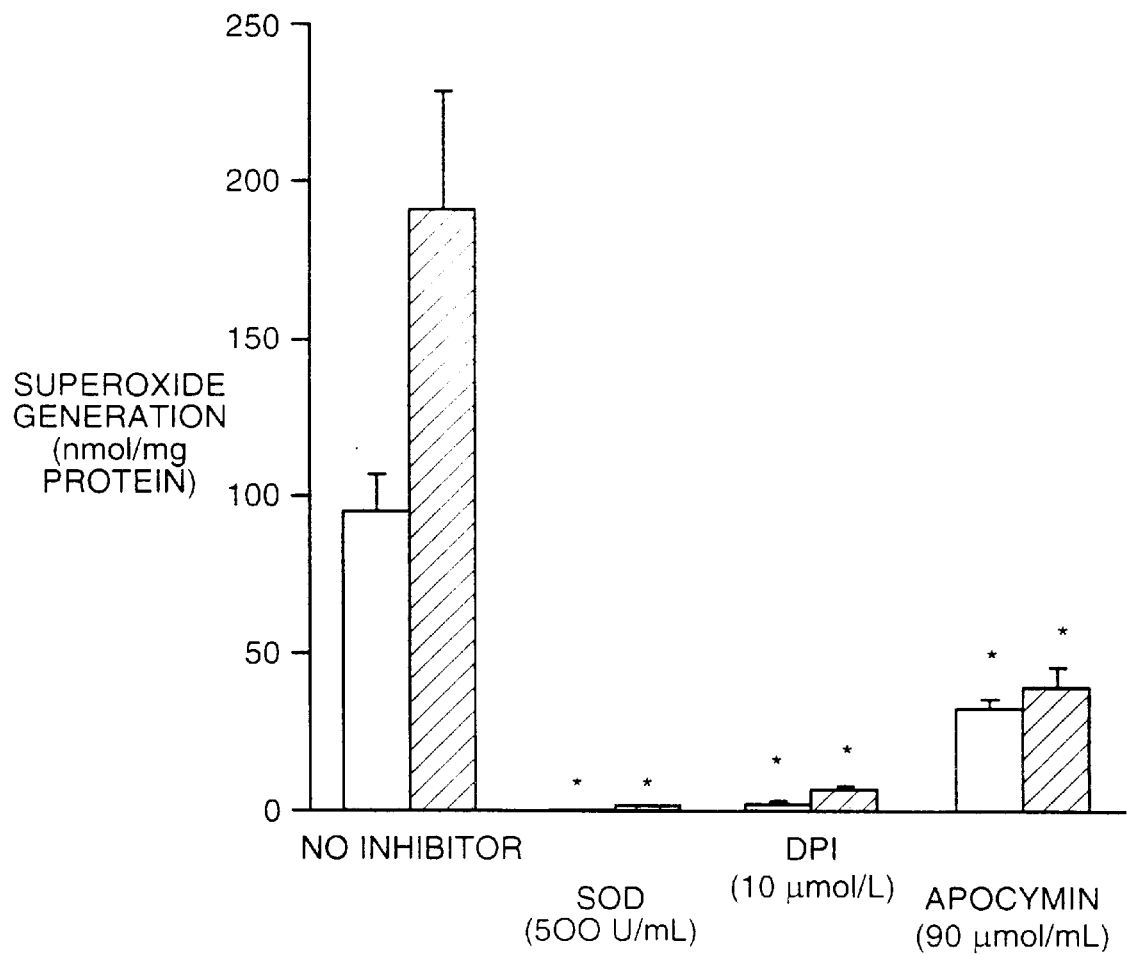
FIG. 12C is a graph showing inhibition of LacCer-induced superoxide generation by various inhibitors.

In FIG. 12C, LacCer induced superoxide generation was reduced by various inhibitors. In FIG. 12C PMNs were first incubated with several inhibitors of ROM for about 15 minutes. These included superoxide dismutase (SOD, 500 U/ml), diphenyleneiodonium chloride (DPI, 10 μM/L) and apocyanin (90 μmol/L). Next the cells were incubated with 100 nmol LacCer for 20 minutes. The generation of superoxide in these cells were measured using lucigenin as a substrate as described above. Data are presented as means +/− SD of three individual experiments. *p<0.01 vs. no inhibitor by Students T-test Hatched boxes represent data from cells treated with no inhibitor and LacCer, or inhibitor and LacCer. Open bars represent cells treated with no inhibitor and no LacCer, or inhibitor and no LacCer.

FIG. 12C shows that LacCer alone (no inhibitor) abrogated superoxide levels about two-fold compared with controls. Pre-incubation with SOD completely abrogated LacCer induced superoxide generation. DPI and apocyanin were relatively less inhibitory with respect to superoxide generation in these PMNs.

In FIG. 11C, PMNs were preincubated with each inhibitor for 15 minutes at room temperature and then stimulated with LacCer for 20 minutes. Superoxide generation was measured for 20 minutes in the absence (open bars) or presence (shaded bars) of 100 nmol/L LacCer. Data are means ± SD of three individual experiments. *p<0.01 vs. no inhibitor by Student's t-test. In that Figure, SOD designates superoxide dismutase, and DPI designates diphenyleneiodonium chloride. The LacCer-induced lucigenin chemiluminescence was blocked by SOD, and inhibited by the NAPDH oxidase inhibitors.

Example 13—Phospholipase $A_2$ Inhibition Inhibited LacCer Upregulation of Mac-1 on PMN The effects of several inhibitors on phospholipase $A_2$ (i.e. $PLA_2$) were evaluated for a role in the LacCer upregulation of Mac-1 in PMNs. It has been proposed that $PLA_2$ is involved in the upregulation of Mac-1 by inflammatory mediators. The involvement of calcium, oxidants, tyrosine kinases or PKC has been suggested in the activation of $PLA_2$.

The prevention of ROM generation (or calcium flux) by NAC or DPI, (or BAPTA/AM), respectively, did not inhibit the LacCer-stimulated Mac-1 upregulation. Moreover, the inhibition of PKC or tyrosine kinase by staurosporine or genistein, respectively, did not inhibit the LacCer upregulation of Mac-1. However, $PLA_2$ inhibition with quinacrine did block this response, in a dose-dependent manner. The effect of PAF-R inhibition was also examined with WEB 2086, because PAF is one of the metabolites downstream of $PLA_2$ which is known to upregulate Mac-1. No significant inhibition was seen (FIGS. 12A–B).

In FIGS. 12A–B, PMNs were first incubated with one of the inhibitors for 20 minutes, and then stimulated with 100 nmol/L LacCer for 20 minutes. The inhibitors tested were DMSO only (vehicle), NAC, DPi, BATPA/AM quinacrine, genistein, staurosporine and WEB 2086. The Mac-1 expression was analyzed by FACScan. Data are presented as mean ± SD (n=3), based on the mean fluorescence of 15000 cells. Dotted lines represent Mac-1 expression without LacCer stimulation. $*p<0.001$, $**p<0.05$ vs. no inhibitor by ANOVA While each of the other agents failed to inhibit PMN Mac-1 expression, only quinacrine substantially inhibited this response.

Figure 13:
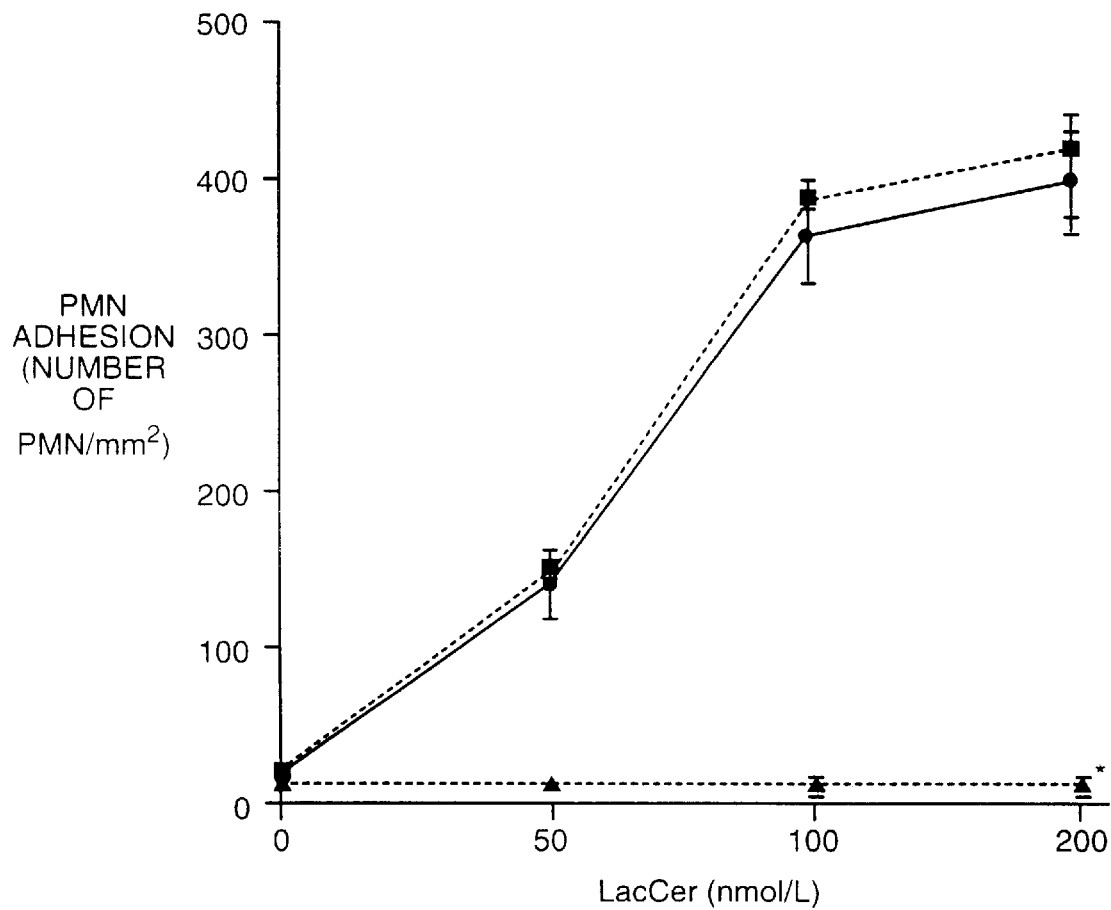
FIG. 13 is a graph showing that LacCer increased PMN adhesion to unstimulated endothelial cells via a CD11b/CD18, Mac-1-dependent mechanism.
Figure 14:
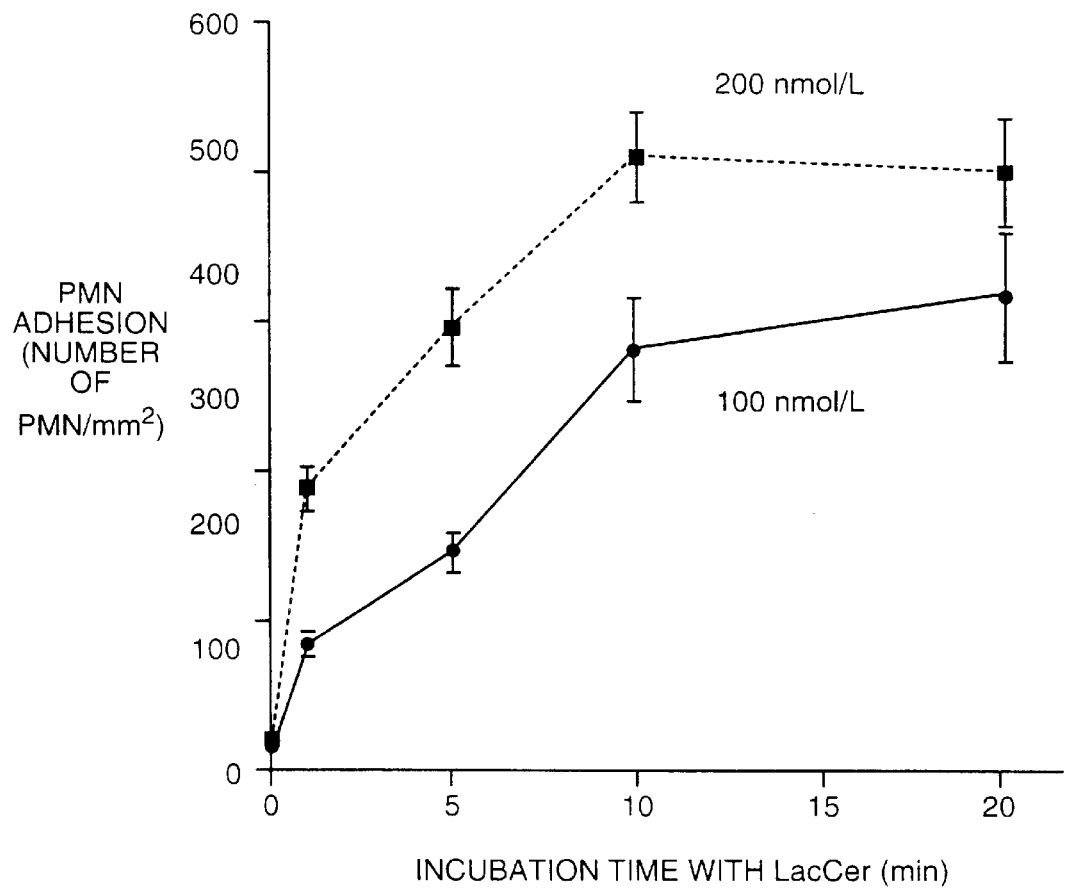
FIG. 14 is a graph showing that LacCer increased PMN adhesion to endothelial cells via a CD11/CD18-dependent mechanism as a function of incubation time with LacCer.
Figure 15:
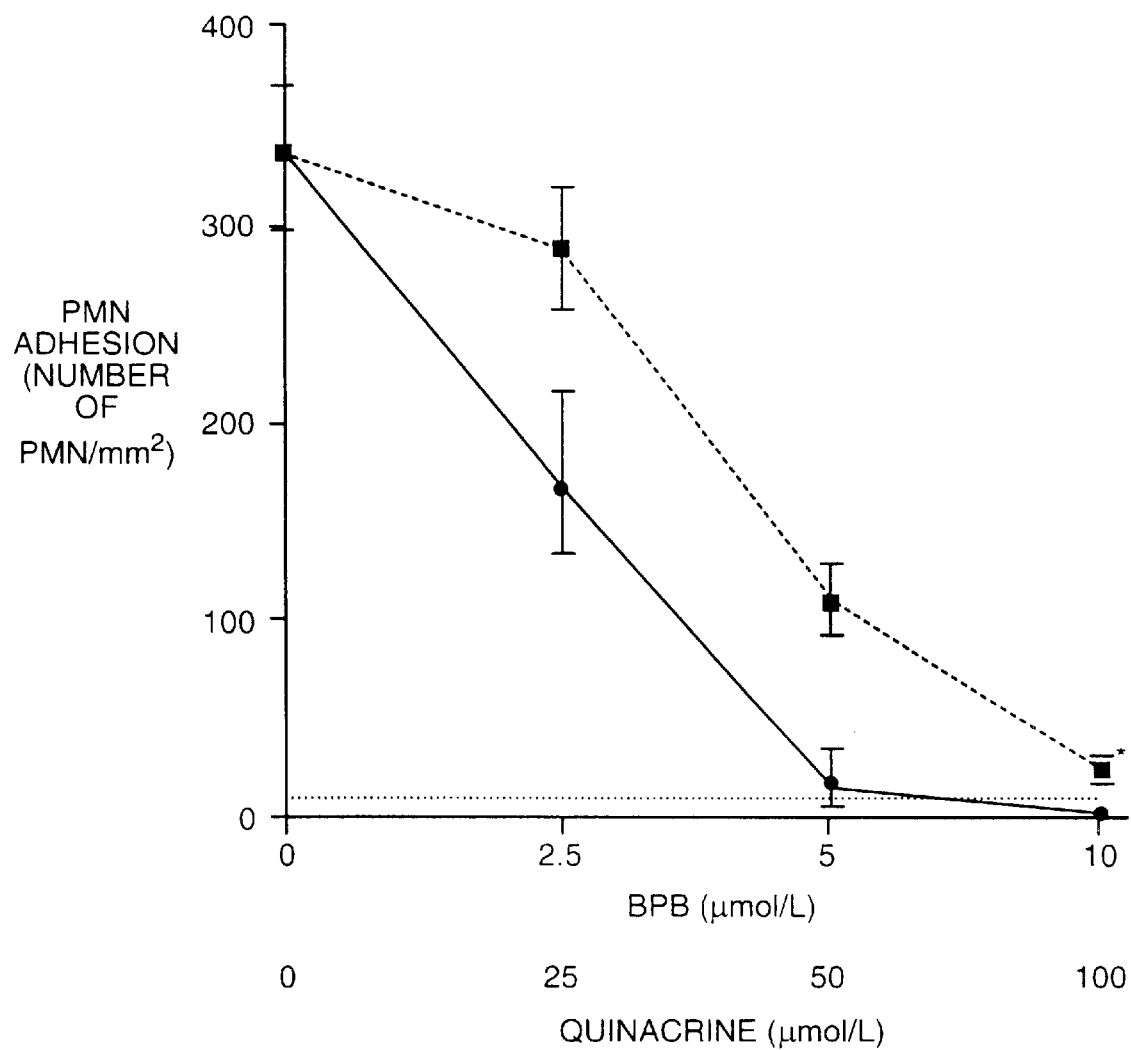
FIG. 15 is a graph depicting quinacrine and bromophenacyl bromide (BPB)-reduced PMN adhesion to endothelial cells.

Example 14—LacCer Increased PMN Adhesion to Unstimulated Endothelial Cells Via a CD11/CD18-dependent Mechanism Incubation of PMNs with LacCer, followed by their repeated washing, increased PMN adhesion to unstimulated ec monolayers in a dose- and time-dependent manner (FIGS. 13–14). Even when these ecs had been prefixed with formaldehyde, the PMN adhesion was comparable to that to the unfixed ecs (FIGS. 10A), indicating that this increment of PMN adhesion was solely PMN dependent, and not due to trace amounts of LacCer carried-over in the medium to the ecs. This PMN adhesion was completely blocked by m-anti-CD18 (FIG. 13), indicating that the LacCer induced PMN adhesion was dependent on CD18. This increase in PMN adhesion was also inhibited by quinacrine, in a dose-dependent manner (FIG. 15), corresponding to the inhibition of Mac-i expression by quinacrine (FIG. 15). In addition, bromophenacyl bromide (BPB) (10 µmol/L) completely abrogated LacCer induced PL-AZ activity and Mac-1 expression in human PMNs.

Isolated PMNs were incubated with increasing concentrations of LacCer for 20 minutes (FIG. 13), or with 100 nmol/L LacCer for varying times (FIG. 14), washed, and then allowed to adhere to unstimulated endothelial cell (ec) monolayers for 30 minutes, followed by washing. LacCer increased PMN adhesion to ec in a dose-(circles in FIG. 13) and time-(FIG. 14) dependent manner. Even when ecs had been pre-fixed with formaldehyde (squares in A), the PMN adhesion was comparable to that to the unfixed ecs (circles in FIG. 13). This increase in PMN adhesion was blocked by anti-CD-18 (triangles in FIG. 13), when the LacCer-treated PMNs were incubated with the antibody (5 µg/ml) before adhesion (FIG. 13). $*p<0.001$ compared to no antibody by Student's t-test.

In FIG. 15, PMNs were first incubated with increasing doses of quinacrine for 20 minutes, then stimulated with 100 nmo/L of LacCer for 20 minutes, followed by washing 3 times, and plated onto formalin-prefixed ec monolayers in the presence of each concentration of quinacrine. Dotted line represents number of adherent PMN without LacCer stimulation. Data are means ± SD for 3 to 6 wells. $*p<0.001$ compared to no quinacrine by ANOVA. The quinacrine dose-dependently inhibited LacCer-induced PMN adhesion.

Example 16—LacCer Increased [$^3$H] Arachidonic Acid Release from Labeled PMNs.

Figure 16:
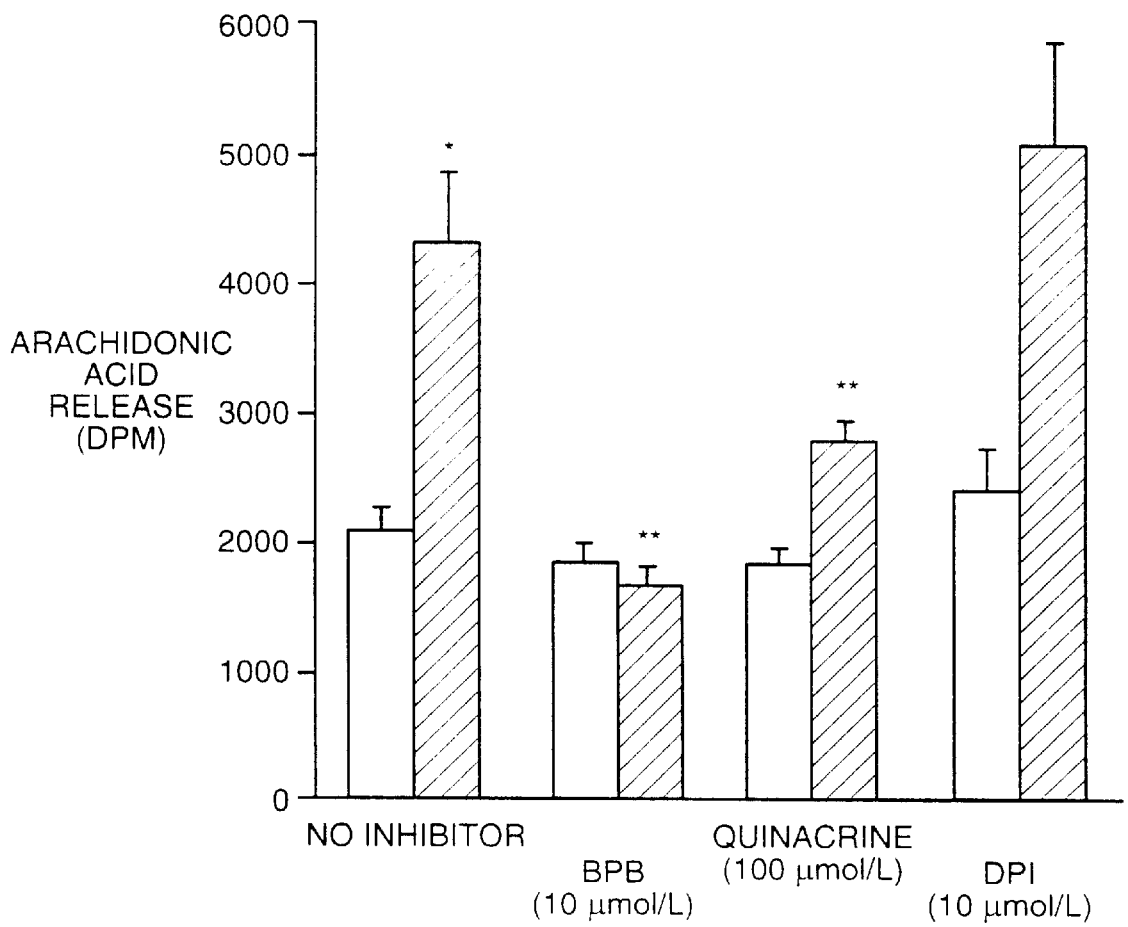
FIG. 16 is a graph showing that LacCer increased [$^3$] arachidoic acid release from labeled PMNs.

PMNs were labeled with [$^3$H] arachidonic acid (AA), and washed serially. These PMNs were incubated with each inhibitor for 15 minutes at room temperature, and then incubated for 30 minutes at 37° C. in the absence (open bars) or presence (shaded bars) of 100 nmol/L LacCer, after which radioactivity of the supernatants was determined. Results are shown in FIG. 16. Data are means ± SD (n=3). $*p<0.01$ vs. no LacCer, $**p<0.01$ vs. no inhibitor, by Student's t-test. In FIG. 16, BPB designates bromophenacyl bromide, and DPI designates diphenylene iodium chloride. LacCer increased [$^3$H] AA release from labeled PMNs, and this was inhibited by phospholipase $A_2$ inhibitors, but not by DPI.

Figure 17:
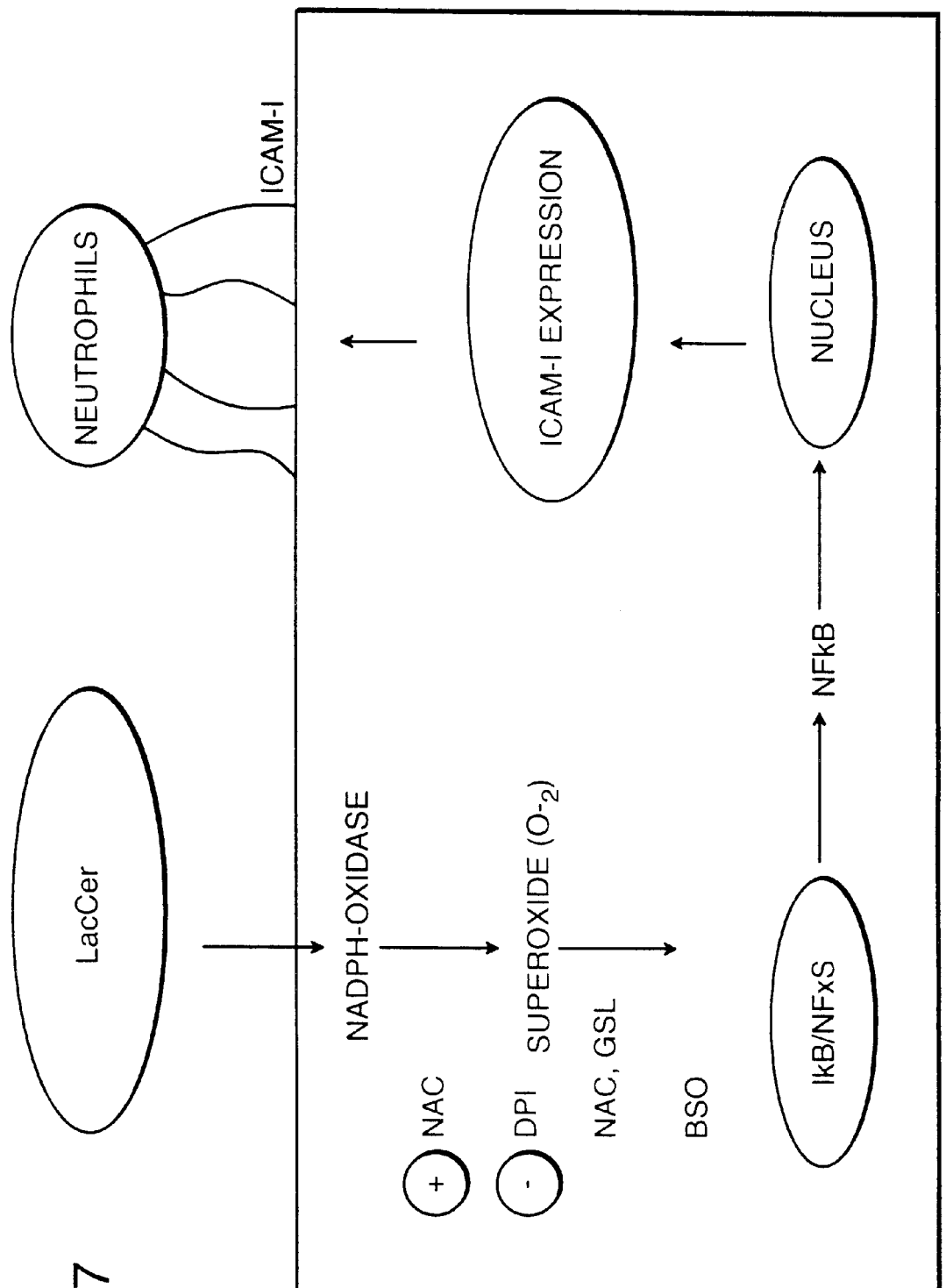
FIG. 17 is a model depicting LacCer-mediated redox signaling leading to ICAM-1 expression in endothelial cells and adhesion to neutrophils.

FIG. 17 shows a model depicting LacCer-mediated redox signaling leading to ICAM-1 expression in endothelial cells and adhesion of neutrophils.

Figure 18:
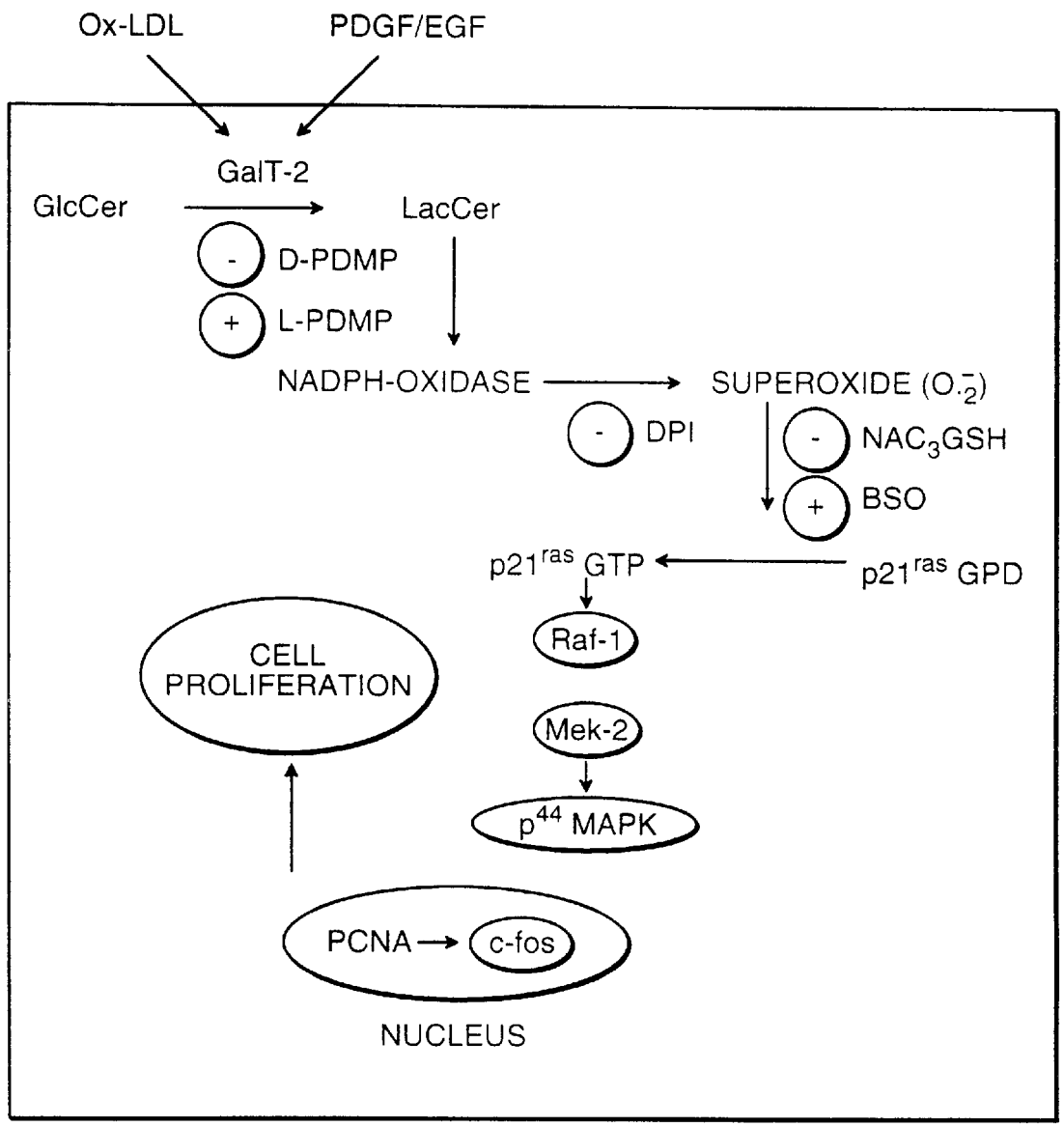
FIG. 18 is a model depicting utilization of Ox-LDL, LacCer, and lipid second messenger in the proliferation of H-ASMC.
Figure 19:
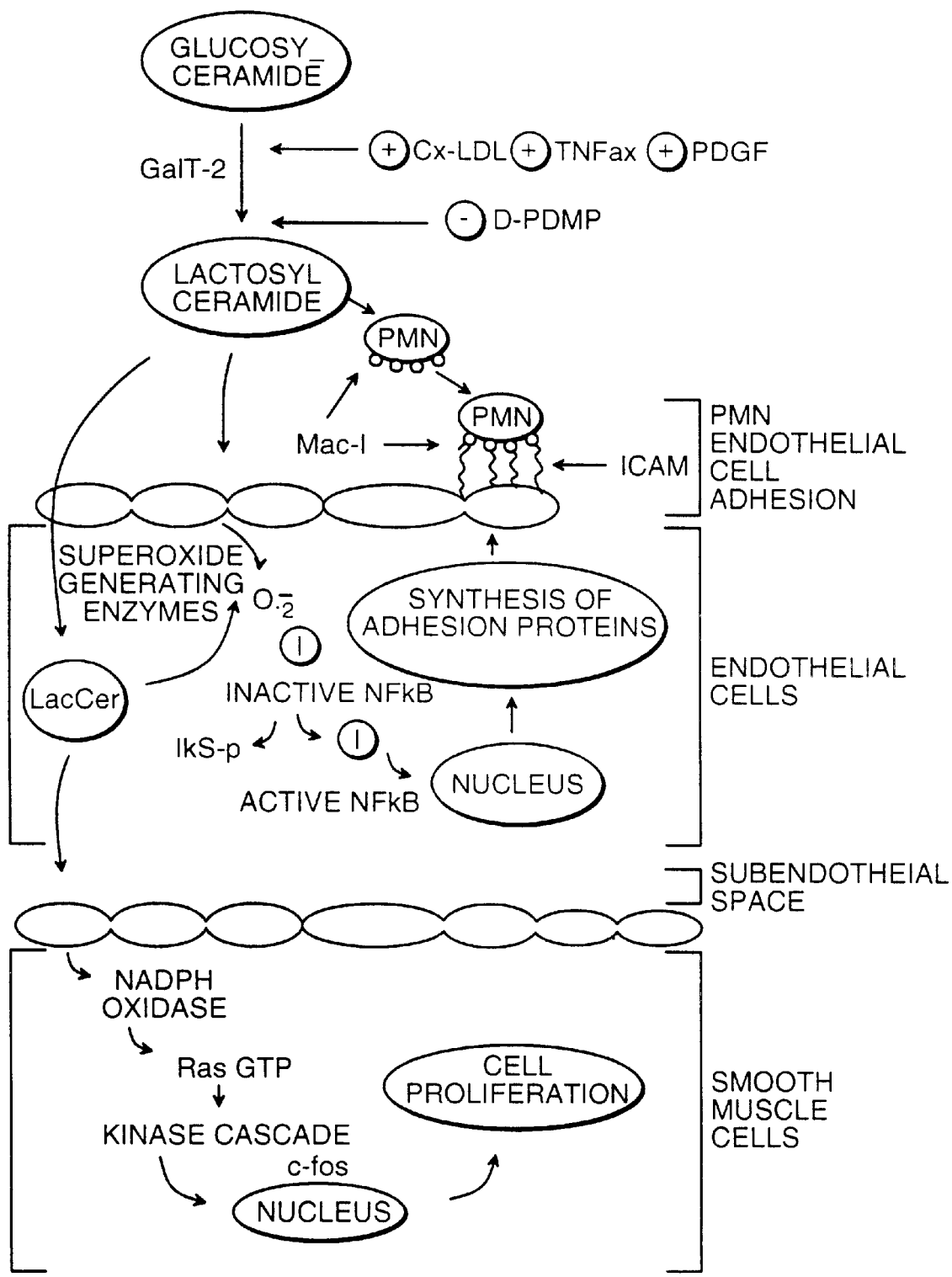
FIG. 19 is a model depicting the role of LacCer as a lipid second messenger and its role in atherosclerosis and use of D-PDMP to abrogate this phenomenon.

FIGS. 18–19 summarize results of examples above and show LacCer-related pathways modulating cell proliferation (FIGS. 18, 19) and cell adhesion (FIG. 19).

The invention has been described in detail with reference to preferred embodiments thereof However, it will be appreciated that those skilled in the art, upon consideration of this disclosure, may make modification and improvements within the spirit and scope of the invention as set forth in the following claims.

What is claimed is:

1. A method for determining the therapeutic capacity of a GalT-2 inhibitor compound to reduce restenosis in a mammal, comprising:

performing an invasive surgical procedure on the mammal;

administering a GalT-2 inhibitor compound to the mammal; and examining a vessel of the mammal for restenosis;

wherein the GalT-2 inhibitor compound is represented by Formula I:

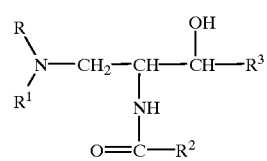

wherein R and $R^1$ are independently selected from the group consisting of hydrogen and straight-chained or branched $C_1$–$C_6$ alkyl with or without a substituent, and further wherein R and $R^1$ may be taken together to form a 5, 6 or 7-membered ring, $R^2$ is selected from the group consisting of branched or straight-chained $C_6$–$C_{30}$ alkyl with or without one to three double bonds, and $R^3$ is selected from the group consisting of straight-chained or branched $C_6$–$C_{20}$ alkyl with or without one to three double bonds and aryl or substituted aryl, where the substituent is halo, $C_1$–$C_4$ alkoxy, methylenedioxy, $C_1$–$C_4$ mercapto, amino or substituted amino in which the amino substituents may suitably be $C_1$–$C_4$ alkyl.

2. A method for determining the therapeutic capacity of a GalT-2 inhibitor compound for treating a disease, post-surgical disorder, or bacterial infection modulated by lactosylceramide, the method comprising:

providing a population of cells responsive to lactosylceramide and comprising an oxidase capable of producing an oxygen species;

contacting the cells with lactosylceramide in an amount sufficient to produce the oxygen species;

culturing the cells in medium comprising a GalT-2 inhibitor compound; and determining effect of the inhibitor compound on amounts of the oxygen species; wherein the GalT-2 inhibitor compound is represented by Formula I:

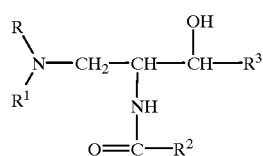

wherein R and $R^1$ are independently selected from the group consisting of hydrogen and straight-chained or branched $C_1$–$C_6$ alkyl with or without a substituent, and further wherein R and $R^1$ may be taken together to form a 5, 6 or 7-membered ring;

$R^2$ is selected from the group consisting of branched or straight-chained $C_6$–$C_{30}$ alkyl with or without one to three double bonds; and $R^3$ is selected from the group consisting of straight-chained or branched $C_6$–$C_{20}$ alkyl with or without one to three double bonds and aryl or substituted aryl, where the substituent is halo, $C_{1-C4}$ alkoxy, methylenedioxy, $C_1$–$C_4$ mercapto, amino or substituted amino in which the amino substituents may suitably be $C_1$–$C_4$ alkyl.

3. A method for determining therapeutic capacity of a GalT-2 inhibitor compound for treating a disease, post-surgical disorder or bacterial infection modulated by lactosylceramide, the method comprising:

providing a population of cells responsive to lactosylceramide, contacting the cells with lactosylceramide in an amount sufficient to enhance loading of an oncogenic protein to a nucleotide triphosphate;

culturing the cells with a GalT-2 inhibitor compound; and determining effect of the inhibitor compound on the oncogenic protein loading to the nucleoside triphosphate;

wherein the GalT-2 inhibitor compound is represented by Formula I:

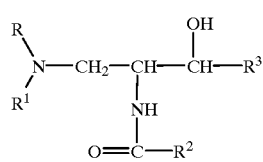

wherein R and $R^1$ are independently selected from the group consisting of hydrogen and straight-chained or branched $C_1$–$C_6$ alkyl with or without a substituent, and further wherein R and $R^1$ may be taken together to form a 5, 6 or 7-membered ring;

$R^2$ is selected from the group consisting of branched or straight-chained $C_6$–$C_{30}$ alkyl with or without one to three double bonds; and $R^3$ is selected from the group consisting of straight-chained or branched $C_6$–$C_{20}$ alkyl with or without one to three double bonds and aryl or substituted aryl, where the substituent is halo, $C_1$–$C_4$ alkoxy, methylenedioxy, $C_1$–$C_4$ mercapto, amino or substituted amino in which the amino substituents may suitably be $C_1$–$C_4$ alkyl.

4. A method for determining therapeutic capacity of a GalT-2 inhibitor compound for treating a disease, post-surgical disorder, or bacterial condition modulated by lactosylceramide, the method comprising:

providing a population of cells responsive to lactosylceramide and comprising a protein kinase cascade comprising a mitogen-activated protein kinase;

contacting the cells with lactosylceramide in an amount sufficient to increase phosphorylation of at least one of the protein kinases in the cascade;

culturing the cells in medium comprising the inhibitor compound; and determining effect of the inhibitor compound on the phosphorylation of the protein kinase;

wherein the GalT-2 inhibitor compound is represented by Formula I:

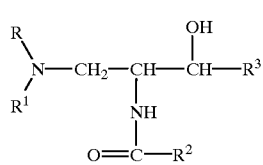

wherein R and $R^1$ are independently selected from the group consisting of hydrogen and straight-chained or branched $C_1$–$C_6$ alkyl with or without a substituent, and further wherein R and $R^1$ may be taken together to form a 5, 6 or 7-membered ring;

$R^2$ is selected from the group consisting of branched or straight-chained $C_6$–$C_{30}$ alkyl with or without one to three double bonds; and $R^3$ is selected from the group consisting of straight-chained or branched $C_6$–$C_{20}$ alkyl with or without one to three double bonds and aryl or substituted aryl, where the substituent is halo, $C_1$–$C_4$ alkoxy, methylenedioxy, $C_1$–$C_4$ mercapto, amino or substituted amino in which the amino substituents may suitably be $C_1$–$C_4$ alkyl.

5. A method for determining therapeutic capacity of a GalT-2 inhibitor compound for treating a disease, post-surgical disorder or bacterial infection modulated by lactosylceramide, the method comprising:

providing a population of cells responsive to lactosylceramide;

contacting the cells with lactosylceramide in an amount sufficient to increase activity of a transcription factor;

culturing the cells in medium comprising the compound; and determining effect of the inhibitor compound on the transcription factor activity;

wherein the GalT-2 inhibitor compound is represented by Formula I:

31

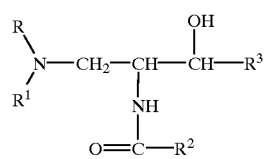

wherein R and $R^1$ are independently selected from the group consisting of hydrogen and straight-chained or branched $C_1$–$C_6$ alkyl with or without a substituent, and further wherein R and $R^1$ may be taken together to form a 5, 6 or 7-membered ring, $R^2$ is selected from the group consisting of branched or straight-chained $C_6$–$C_{30}$ alkyl with or without one to three double bonds; and $R^3$ is selected from the group consisting of straight-chained or branched $C_6$–$C_{20}$ alkyl with or without one to three double bonds and aryl or substituted aryl, where the substituent is halo, $C_1$–$C_4$ alkoxy, methylenedioxy, $C_1$–$C_4$ mercapto, amino or substituted amino in which the amino substituents may suitably be $C_1$–$C_4$ alkyl.

6. A method for determining therapeutic capacity of a GalT-2 inhibitor compound for treating a disease, post-surgical disorder, or bacterial infection modulated by lactosylceramide, the method comprising:

providing a first population of cells responsive to lacto-sylceramide and capable of expressing a receptor which binds an adhesion molecule;

contacting the cells with lactosylceramide in an amount sufficient to increase expression of the receptor in the cells;

culturing the cells in medium comprising the compound;

contacting the cells with a second population of cells expressing the adhesion molecule; and determining effect of the inhibitor compound on the adhesion wherein the GalT-2 inhibitor compound is represented by Formula I:

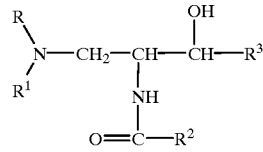

wherein R and $R^1$ are independently selected from the group consisting of hydrogen and straight-chained or branched $C_1$–$C_6$ alkyl with or without a substituent, and further wherein R and $R^1$ may be taken together to form a 5, 6 or 7-membered ring;

$R^2$ is selected from the group consisting of branched or straight-chained $C_6$–$C_{30}$ alkyl with or without one to three double bonds; and R3 is selected from the group consisting of straight-chained or branched $C_6$–$C_{20}$ alkyl with or without one to three double bonds and aryl or substituted aryl, where the substituent is halo, $C_1$–$C_4$ alkoxy, methylenedioxy, $C_1$–$C_4$ mercapto, amino or substituted amino in which the amino substituents may suitably be $C_1$–$C_4$ alkyl.

7. A method for determining therapeutic capacity of a GalT-2 inhibitor compound for treating a bacterial infection modulated by binding of a bacterial toxin to lactosylceramide, the method comprising:

providing a population of cells responsive to lactosylce-ramide;

contacting the cells with a bacterial toxin capable of binding the lactosylceramide;

culturing the cells in medium comprising the compound; and determining any effect of the inhibitor compound on the cell viability wherein the GalT-2 inhibitor compound is represented by Formula I:

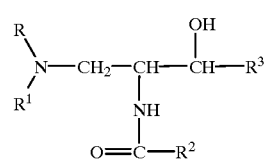

wherein R and $R^1$ are independently selected from the group consisting of hydrogen and straight-chained or branched $C_1$–$C_6$ alkyl with or without a substituent, and further wherein R and $R^1$ may be taken together to form a 5, 6 or 7-membered ring;

$R^2$ is selected from the group consisting of branched or straight-chained $C_6$–$C_{30}$ alkyl with or without one to three double bonds; and $R^3$ is selected from the group consisting of straight-chained or branched $C_6$–$C_{20}$ alkyl with or without one to three double bonds and aryl or substituted aryl, where the substituent is halo, $C_1$–$C_4$ alkoxy, methylenedioxy, $C_1$–$C_4$ mercapto, amino or substituted amino in which the amino substituents may suitably be $C_1$–$C_4$ alkyl.

8. A method for determining the therapeutic capacity of a GalT-2 inhibitor compound for treating a disease, post-surgical disorder, or bacterial infection modulated by lactosylceramide, the method comprising:

providing a population of cells responsive to lactosylce-ramide and comprising a cell proliferation factor;

contacting the cells with lactosylceramide in an amount sufficient to decrease activity of the cell proliferation factor;

culturing the cells in medium comprising the GalT-2 inhibitor compound; and determining effect of the inhibitor compound on the levels of the cell prolifera-tion factor;

wherein the GalT-2 inhibitor compound is represented by Formula I:

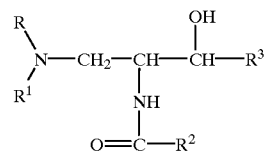

wherein R and $R^1$ are independently selected from the group consisting of hydrogen and straight-chained or branched $C_1$–$C_6$ alkyl with or without a substituent, and further wherein R and $R^1$ may be taken together to form a 5, 6 or 7-membered ring;

$R^2$ is selected from the group consisting of branched or straight-chained $C_6$–$C_{30}$ alkyl with or without one to three double bonds; and $R^3$ is selected from the group consisting of straight-chained or branched $C_6$–$C_{20}$ alkyl with or without one to three double bonds and aryl or substituted aryl, where the substituent is halo, $C_1$-$C_4$ alkoxy, methylenedioxy, $C_1$–$C_4$ mercanto, amino or substituted amino in which the amino substituents may suitably be $C_1$–$C_4$ alkyl.

* * * * *